United States Patent
Naveh et al.

(10) Patent No.: US 11,744,694 B2
(45) Date of Patent: Sep. 5, 2023

(54) METHODS AND ASSEMBLIES FOR DEPLOYING BILIARY STENTS

(71) Applicant: ENDO GI MEDICAL LTD., Nazareth (IL)

(72) Inventors: Omri Naveh, Ramat Yshay (IL); Elad Einav, Salit (IL); Ronny Barak, Tel Aviv (IL)

(73) Assignee: ENDO GI MEDICAL LTD., Nazareth (IL)

( * ) Notice: Subject to any disclaimer, the term of this patent is extended or adjusted under 35 U.S.C. 154(b) by 215 days.

(21) Appl. No.: 17/140,001

(22) Filed: Jan. 1, 2021

(65) Prior Publication Data
US 2021/0196444 A1   Jul. 1, 2021

Related U.S. Application Data

(60) Provisional application No. 63/078,539, filed on Sep. 15, 2020, provisional application No. 62/956,294, filed on Jan. 1, 2020.

(51) Int. Cl.
*A61F 2/04* (2013.01)
*A61M 25/09* (2006.01)
(Continued)

(52) U.S. Cl.
CPC .......... *A61F 2/04* (2013.01); *A61F 2002/041* (2013.01); *A61F 2002/826* (2013.01); *A61F 2002/9505* (2013.01); *A61M 25/09* (2013.01)

(58) Field of Classification Search
CPC .................. A61F 2/04; A61F 2002/041; A61F 2002/826; A61F 2002/9505;
(Continued)

(56) References Cited

U.S. PATENT DOCUMENTS 4,781,690 A * 11/1988 Ishida ............... A61L 31/06
  604/528
4,874,374 A * 10/1989 Kousai ............. B29C 48/335
  604/528

(Continued)

FOREIGN PATENT DOCUMENTS

AU   2006335685 A1   9/2007
AU   2020201370 A1   3/2020
(Continued)

OTHER PUBLICATIONS

Machine Translation (Google Patents) for JP5687216 published on Mar. 18, 2015 Bolton Medical Inc.
(Continued)

*Primary Examiner* — Paul B Prebilic
(74) *Attorney, Agent, or Firm* — Momentum IP; Marc Van Dyke

(57) ABSTRACT

A stent-deployment assembly for use with a guidewire comprises a biliary stent and an elongated stent-conveyance tube comprising a guidewire-retaining segment that includes respective distal and proximal apertures defining a guidewire-path therethrough, and a lengthways laterally-breachable portion. In a stent-advancement configuration, the guidewire passes through the respective apertures so as to interiorly traverse the guidewire-retaining segment, and the stent is arranged to surround a stent-conveyance tube segment that is proximally displaced from the guidewire-retaining segment, for advancement of the stent together with the stent-conveyance tube along the guidewire into a body lumen of a human subject. When the stent is disposed, in the stent-advancement configuration, at a target deployment location within the lumen, a proximal-direction withdrawal of the stent-conveyance tube is effective to cause the guidewire to breach the laterally-breachable portion of the (Continued)

guidewire-retaining segment so as to decouple the guidewire from the tube without longitudinal displacement of the guidewire.

14 Claims, 18 Drawing Sheets

(51) Int. Cl.
*A61F 2/95* (2013.01)
*A61F 2/82* (2013.01)

(58) Field of Classification Search
CPC ...... A61F 2220/0075; A61F 2250/0026; A61F 2250/0036; A61F 2250/0039; A61F 2250/0071
See application file for complete search history.

(56) References Cited

U.S. PATENT DOCUMENTS

| | | | |
|---|---|---|---|
| 5,669,924 A | 9/1997 | Shaknovich | |
| 6,299,595 B1 | 10/2001 | Dutta | |
| 6,346,093 B1* | 2/2002 | Allman | A61M 25/0097 604/164.03 |
| 7,637,863 B2 | 12/2009 | Deal | |
| 7,691,125 B2 | 4/2010 | Ducharme | |
| 7,963,987 B2 | 6/2011 | Melsheimer | |
| 7,967,830 B2 | 6/2011 | Ayala | |
| 8,206,320 B2 | 6/2012 | Deal | |
| 8,211,087 B2 | 7/2012 | Carter | |
| 8,512,389 B2 | 8/2013 | Ayala | |
| 8,591,563 B2 | 11/2013 | Karpiel | |
| 8,690,756 B2 | 4/2014 | Deal | |
| 8,955,520 B2 | 2/2015 | Devereux | |
| 9,095,466 B2 | 8/2015 | Norris | |
| 9,402,755 B2 | 8/2016 | Norris | |
| 9,510,962 B2 | 12/2016 | Aoba | |
| 2001/0044622 A1 | 11/2001 | Vardi | |
| 2005/0085891 A1* | 4/2005 | Goto | A61F 2/95 623/1.11 |
| 2005/0125050 A1 | 6/2005 | Carter | |
| 2005/0143770 A1 | 6/2005 | Carter | |
| 2005/0222603 A1 | 10/2005 | Andreas | |
| 2009/0171427 A1 | 7/2009 | Melsheimer | |
| 2010/0121426 A1 | 5/2010 | Howell | |
| 2011/0087234 A1 | 4/2011 | Ayala | |
| 2013/0030416 A1 | 1/2013 | Fernandes | |
| 2014/0188210 A1 | 7/2014 | Beard | |
| 2015/0011834 A1 | 1/2015 | Ayala | |
| 2019/0000652 A1 | 1/2019 | Einav | |
| 2021/0196444 A1 | 7/2021 | Naveh | |
| 2021/0259867 A1 | 8/2021 | Einav | |
| 2022/0008234 A1 | 1/2022 | Einav | |

FOREIGN PATENT DOCUMENTS

| | | |
|---|---|---|
| AU | 2020250291 A1 | 11/2020 |
| CA | 2597424 A1 | 8/2007 |
| EP | 1867305 A2 | 12/2007 |
| EP | 2278939 B1 | 4/2021 |
| JP | 2012152344 A | 8/2012 |
| JP | 5687216 B2 | 3/2015 |
| WO | 2005/011530 A1 | 2/2005 |
| WO | 2005/011788 A1 | 2/2005 |
| WO | 2005/011790 A1 | 2/2005 |
| WO | 2005/011791 A2 | 2/2005 |
| WO | 2005011530 A1 | 2/2005 |
| WO | 2005011788 A1 | 2/2005 |
| WO | 2005011790 A1 | 2/2005 |
| WO | 2005011791 A2 | 2/2005 |
| WO | 2005/107842 A1 | 11/2005 |
| WO | 2005107842 A1 | 11/2005 |
| WO | 2006/015323 A2 | 2/2006 |
| WO | 2006015323 A3 | 2/2006 |
| WO | 2017/109783 A1 | 6/2017 |
| WO | 2020/003316 A1 | 1/2020 |

OTHER PUBLICATIONS

Machine Translation (Google Patents) for JP2012152344 published on Aug. 16, 2012 Terumo Corp.
International Search Report for PCT/IL2016/051368 dated Oct. 2, 2017.
Written Opinion for PCT/IL2016/051368 dated Oct. 2, 2017.
International Search Report for PCT/IL2019/050713 dated Oct. 4, 2019.
Written Opinion for PCT/IL2019/050713 dated Oct. 4, 2019.
Machine Translation (Google Patents) for JP201252344 published Aug. 16, 2012 Terumo Corp.

* cited by examiner

METHODS AND ASSEMBLIES FOR DEPLOYING BILIARY STENTS

FIELD OF THE INVENTION

Embodiments of the present invention relate generally to medical devices and more particularly to methods and apparatus for deploying stents in a lumen of a subject.

BACKGROUND

Stents are typically deployed within a lumen of a body of a subject for various reasons. In some cases, a stent is deployed within a lumen in order to widen a narrowed section of the lumen. For example, insertion of a biliary stent into a bile duct is used to treat obstructions and strictures that occur in the bile duct. There are several conditions, malignant or benign, that can cause strictures of the bile duct. Pancreatic cancer is a common malignant cause of strictures of the bile duct. Noncancerous causes of bile duct stricture may include injury to the bile duct that occurs during surgery for gallbladder removal, and pancreatitis.

A biliary stent is typically a tube-like structure that is used to support a narrowed part of the bile duct and inhibit the reformation of the stricture. A tube or catheter is often used to deploy stents, and a guidewire is often used to aid in guiding the stent to its targeted deployment location within the lumen. Manipulation of the guidewire in a stage of deployment of the stent can cause fracturing of the guidewire and/or have other adverse physical impacts on the subject. Therefore there is a need for a reliable method and device for deploying biliary stents which do not require manipulating the guidewire.

SUMMARY

Embodiments of the invention relate to apparatus including a biliary stent and a stent-conveyance tube. The apparatus may be provided in an assembled form (e.g. the stent is mounted to the tube) or in kit form.

One salient feature provided by certain embodiments of the invention that is only a single stent is provided—e.g. only a single stent mounted to the tube or only a single stent is included in the kit. This single stent is the aforementioned biliary stent.

Specific features related to packaging, provided by specific embodiments, are also disclosed and claimed herein.

Apparatus for use with a guidewire, comprising: a. a biliary stent; and b. an elongated stent-conveyance tube comprising a guidewire-retaining segment that includes (i) respective distal and proximal apertures defining a guidewire-path therethrough, and (ii) a lengthways laterally-breachable portion, wherein: i. in a stent-advancement configuration, (A) the guidewire passes through the respective apertures so as to interiorly traverse the guidewire-retaining segment, and (B) the stent is arranged to surround a stent-conveyance tube segment that is proximally displaced from the guidewire-retaining segment, for advancement of the stent together with the stent-conveyance tube along the guidewire into a body lumen of a human subject, and ii. when the stent is disposed, in the stent-advancement configuration, at a target deployment location within the lumen, a proximal-direction withdrawal of the stent-conveyance tube is effective to cause the guidewire to breach the laterally-breachable portion of the guidewire-retaining segment so as to decouple the guidewire from the tube without longitudinal displacement of the guidewire.

In some embodiments, in the stent-advancement configuration the stent is the only stent engaged with the guidewire.

In some embodiments, wherein the apparatus comprises only a single stent that is the biliary stent.

In some embodiments, provided as an assembled configuration such that (i) the single biliary stent is mounted to the stent-conveyance tube; and (ii) no stent other than the single biliary stent is engaged to the stent-conveyance tube.

In some embodiments, (e.g. provided in the stent-advancement configuration and) further comprising the guidewire which is engaged to and in contact with the single biliary stent.

In some embodiments, in the stent-advancement configuration the guidewire does not interiorly traverse the tube segment surrounded by the stent.

In some embodiments, both the single biliary stent and the stent-conveyance tube that is mounted thereto are disposed within a common container, the container being closed.

In some embodiments, no other stent other than the biliary stent is present within the common container.

In some embodiments, provided in a kit form so that the single biliary stent is not mounted to the stent-conveyance tube, wherein both the single biliary stent and the stent-conveyance tube both are disposed within a common and closed container, and no other stent is disposed within the container.

In some embodiments, wherein the common container is a pouch.

In some embodiments, an interior of the common container is sterile or pre-sterilized.

In some embodiments, wherein the common container is sealed.

In some embodiments, provided in a kit form such that the stent-conveyance tube is disposed within a closed container without any stent mounted thereto, an interior thereof being sterile or sterilized.

In some embodiments, provided in a kit form so that the single biliary stent is not mounted to the stent-conveyance tube, wherein the biliary and stent-conveyance tube are disposed within respective closed containers that are mechanically engaged to each other, and no other stent is mechanically engaged to either container.

In some embodiments, wherein (e.g. see FIG. 2B) a plurality of distinct slits are longitudinally disposed along the guidewire-retaining segment, the slits being longitudinally spaced from each other so that the slits and non-slit portions of the guidewire-retaining segment longitudinally alternate with each other.

In some embodiments, wherein (e.g. see FIG. 2B) a plurality of distinct pre-weakened sections are longitudinally disposed along the guidewire-retaining segment, the pre-weakened sections being longitudinally spaced from each other so that the pre-weakened sections and non-pre-weakened portions of the guidewire-retaining segment longitudinally alternate with each other.

In some embodiments, wherein (e.g. see FIG. 2B) a plurality of distinct thinned-tube-wall sections are longitudinally disposed along the guidewire-retaining segment, the thinned-tube-wall sections being longitudinally spaced from each other so that the thinned tube-wall sections and sections where the tube-wall is thicker of the guidewire-retaining segment longitudinally alternate with each other.

In some embodiments, a proximal-direction withdrawal of the stent-conveyance tube effective to cause the guidewire to breach the laterally-breachable portion of the guidewire-retaining segment can be effected by applying a first proximal-withdrawal force of at least 100 grams and no more than 20 kg, or at least 500 grams and no more than 10 kg, or at least 1 kg and no more than 5 kg, or at least 1.5 kg and no more than 2.5 kg.

In some embodiments, wherein a proximal-direction withdrawal of the stent-conveyance tube after the lateral breaching of the laterally-breachable portion of the guidewire-retaining segment by the guidewire can be effected by a second proximal-withdrawal force, lesser than the first proximal-withdrawal force. In some embodiments, wherein the proximal-direction withdrawal of the stent-conveyance tube effective to leave the stent deployed in the lumen without manipulation of the guidewire.

In some embodiments, wherein in the stent-advancement configuration the guidewire does not interiorly traverse the tube segment surrounded by the stent.

In some embodiments, wherein the laterally-breachable portion of the guidewire-retaining segment includes at least one of: (i) a slit having opposed slit-lips and (b) a perforation and (iii) a thinned tube-wall.

In some embodiments, wherein (i) the stent is a first stent, and the apparatus additionally comprises a second stent, and (ii) in the stent-advancement configuration (A) the second stent is arranged to surround a second stent-conveyance tube segment proximally displaced from the first stent, for advancement of the second stent into the body lumen, and (B) the guidewire interiorly traverses the second stent-conveyance tube segment.

A method for assembly comprising: a. providing a guidewire, a biliary stent and a stent-conveyance tube, the stent-conveyance tube having a guidewire-retaining segment and a stent-conveyance tube segment proximally displaced therefrom; b. arranging the biliary stent around the stent-conveyance tube segment; and c. passing an end-section of a guidewire through respective distal and proximal apertures of the guidewire-retaining segment so as to interiorly traverse the guidewire-retaining segment, the guidewire-retaining segment having a lengthways laterally-breachable portion, wherein the passing through and arranging are effective in combination to achieve an assembled state in which the stent-conveyance tube is longitudinally advanceable along the guidewire together with the stent arranged therearound, the guidewire-retaining segment being effective to retain the guidewire therewithin; and the stent-deployment assembly is operative to be disassembled by anchoring the stent, and, with the stent anchored, proximally withdrawing the stent-conveyance tube at least from the interior of the stent without manipulating the guidewire, the proximal withdrawing of the tube being effective to cause the guidewire to laterally breach the laterally-breachable portion of the guidewire-retaining segment and thereby to decouple the guidewire from the tube.

In some embodiments, in the stent-advancement configuration the stent is the only stent engaged with the guidewire.

In some embodiments, upon completion of the method, only a single stent that is the biliary stent is mounted to the stent-conveyance tube; and (ii) no stent other than the single biliary stent is engaged to the stent-conveyance tube.

In some embodiments, wherein step (b) is performed before step (c).

In some embodiments, wherein step (c) is performed before step (b).

In some embodiments, wherein: the proximal withdrawing of the tube includes applying a first proximal-withdrawal force effective to cause the guidewire to laterally breach the laterally-breachable portion of the guidewire-retaining segment, the first proximal-withdrawal force being at least 100 grams and no more than 10 kg, or at least 500 grams and no more than 5 kg, or at least 1 kg and no more than 2.5 kg, or at least 1.5 kg and no more than 2 kg, and a second proximal-withdrawal force, lesser than the first proximal-withdrawal force, is effective to withdraw the stent-conveyance tube from the stent after the lateral breaching of the laterally-breachable portion of the guidewire-retaining segment by the guidewire.

In some embodiments, wherein in the stent-advancement configuration the guidewire does not interiorly traverse the tube segment surrounded by the stent.

In some embodiments, wherein (i) the stent is a first stent, and the stent-conveyance tube segment is a first stent-conveyance tube segment, and (ii) the method additionally comprises: arranging a second stent to surround a second stent-conveyance tube segment that is proximally displaced from the first stent-conveyance tube segment; and passing the proximal end-section of the guidewire through an aperture disposed proximally from the first stent-conveyance tube segment and distally from the second stent-conveyance tube segment, such that that the guidewire interiorly traverses the second stent-conveyance tube segment.

In some embodiments, wherein (e.g. see FIG. 2B) a plurality of distinct slits are longitudinally disposed along the guidewire-retaining segment, the slits being longitudinally spaced from each other so that the slits and non-slit portions of the guidewire-retaining segment longitudinally alternate with each other.

In some embodiments, wherein (e.g. see FIG. 2B) a plurality of distinct pre-weakened sections are longitudinally disposed along the guidewire-retaining segment, the pre-weakened sections being longitudinally spaced from each other so that the pre-weakened sections and non-pre-weakened portions of the guidewire-retaining segment longitudinally alternate with each other.

According to embodiments disclosed herein, a stent-deployment assembly for use with a guidewire comprises: (a) a biliary stent; and (b) an elongated stent-conveyance tube comprising a guidewire-retaining segment that includes (i) respective distal and proximal apertures defining a guidewire-path therethrough, and (ii) a lengthways laterally-breachable portion. The assembly is characterized as follows: (i) in a stent-advancement configuration, (A) the guidewire passes through the respective apertures so as to interiorly traverse the guidewire-retaining segment, and (B) the stent is arranged to surround a stent-conveyance tube segment that is proximally displaced from the guidewire-retaining segment, for advancement of the stent together with the stent-conveyance tube along the guidewire into a body lumen of a human subject, and (ii) when the stent is disposed, in the stent-advancement configuration, at a target deployment location within the lumen, a proximal-direction withdrawal of the stent-conveyance tube is effective to cause the guidewire to breach the laterally-breachable portion of the guidewire-retaining segment so as to decouple the guidewire from the tube without longitudinal displacement of the guidewire.

In some embodiments, it can be that when the assembly is advanced along the guidewire in the stent-advancement configuration, the guidewire-retaining segment is effective to retain the guidewire within.

In some embodiments, in the stent-advancement configuration, it can be that the guidewire does not interiorly traverse the tube segment surrounded by the stent.

In some embodiments, a segment of the stent-conveyance tube proximally abutting the guidewire-retaining segment can have a smaller diameter than does the guidewire-retaining segment.

In some embodiments, it can be that the distal aperture of the guidewire-retaining segment faces distally and the proximal aperture faces proximally.

In some embodiments, the assembly can additionally comprise a proximally withdrawable locking mechanism effective to maintain a position of the stent relative to the tube when the assembly is advanced along the guidewire in the stent-advancement configuration.

In some embodiments, it can be that a proximal-direction withdrawal of the stent-conveyance tube effective to cause the guidewire to breach the laterally-breachable portion of the guidewire-retaining segment can be effected by applying a first proximal-withdrawal force of at least 100 grams and no more than 20 kg, or at least 500 grams and no more than 10 kg, or at least 1 kg and no more than 5 kg, or at least 1.5 kg and no more than 2.5 kg. In some embodiments, it can be that a proximal-direction withdrawal of the stent-conveyance tube after the lateral breaching of the laterally-breachable portion of the guidewire-retaining segment by the guidewire can be effected by a second proximal-withdrawal force, lesser than the first proximal-withdrawal force. In some embodiments, the proximal-direction withdrawal of the stent-conveyance tube after the lateral breaching of the laterally-breachable portion of the guidewire-retaining segment by the guidewire can be effective to leave the stent deployed in the lumen without manipulation of the guidewire.

In some embodiments, the laterally-breachable portion of the guidewire-retaining segment can include a slit portion having opposed slit-lips either in contact with each other or displaced from each other by no more than a diameter of the guidewire. In some embodiments, the laterally-breachable portion of the guidewire-retaining segment can include a perforated and/or thinned tube-wall portion.

In some embodiments, the assembly can additionally comprise the guidewire.

In some embodiments, in the stent-advancement configuration, the stent can be the only stent engaged with the guidewire.

In some embodiments, it can be that (i) the stent is a first stent, and the assembly additionally comprises a second stent, and (ii) in the stent-advancement configuration the second stent is arranged to surround a second stent-conveyance tube segment proximally displaced from the first stent, for advancement of the second stent into the body lumen. In some such embodiments, in the stent-advancement configuration, the guidewire can interiorly traverse the second stent-conveyance tube segment.

In some such embodiments, it can be that when the second stent is disposed at a second target deployment location alongside the deployed first stent, a proximal-direction withdrawal of the stent-conveyance tube and of the guidewire is effective to leave the stent deployed in the lumen without further manipulation of the guidewire.

According to embodiments disclosed herein, a stent-deployment assembly for use with a guidewire comprises: (a) an elongated stent-conveyance tube comprising a guidewire-retaining segment (i) having a lengthways laterally-breachable portion and (ii) configured for having the guidewire traverse therethrough; and (b) a biliary stent arranged to surround a stent-conveyance tube segment that is proximally displaced from the guidewire-retaining segment, for advancement of the stent together with the stent-conveyance tube along the guidewire into a body lumen of a human subject. The assembly is characterized as follows: when the stent is disposed at a target deployment location within the lumen, a proximal-direction withdrawal of the stent-conveyance tube is effective to cause the guidewire to breach the laterally-breachable portion of the guidewire-retaining segment so as to decouple the guidewire from the tube without manipulation of the guidewire.

In some embodiments, it can be that when the assembly is advanced along the guidewire in the stent-advancement configuration, the guidewire-retaining segment is effective to retain the guidewire within.

In some embodiments, it can be that in the stent-advancement configuration, the guidewire does not interiorly traverse the tube segment surrounded by the stent.

In some embodiments, a segment of the stent-conveyance tube proximally abutting the guidewire-retaining segment can have a smaller diameter than does the guidewire-retaining segment.

In some embodiments, the assembly can additionally comprise a proximally withdrawable locking mechanism effective to maintain a position of the stent relative to the tube when the assembly is advanced along the guidewire in the stent-advancement configuration.

In some embodiments, it can be that a proximal-direction withdrawal of the stent-conveyance tube effective to cause the guidewire to breach the laterally-breachable portion of the guidewire-retaining segment can be effected by applying a first proximal-withdrawal force of at least 100 grams and no more than 20 kg, or at least 500 grams and no more than 10 kg, or at least 1 kg and no more than 5 kg, or at least 1.5 kg and no more than 2.5 kg. In some such embodiments, a proximal-direction withdrawal of the stent-conveyance tube after the lateral breaching of the laterally-breachable portion of the guidewire-retaining segment by the guidewire can be effected by a second proximal-withdrawal force, lesser than the first proximal-withdrawal force.

In some embodiments, it can be that wherein the proximal-direction withdrawal of the stent-conveyance tube after the lateral breaching of the laterally-breachable portion of the guidewire-retaining segment by the guidewire is effective to leave the stent deployed in the lumen without manipulation of the guidewire.

In some embodiments, it can be that the laterally-breachable portion of the guidewire-retaining segment includes a slit portion having opposed slit-lips either in contact with each other or displaced from each other by no more than a diameter of the guidewire. In some embodiments, the laterally-breachable portion of the guidewire-retaining segment can include a perforated and/or thinned tube-wall portion.

In some embodiments, the assembly can additionally comprise the guidewire.

In some embodiments, it can be that in the stent-advancement configuration, the stent is the only stent engaged with the guidewire.

In some embodiments, it can be that (i) the stent is a first stent, and the assembly additionally comprises a second stent, and (ii) in the stent-advancement configuration the second stent is arranged to surround a second stent-conveyance tube segment proximally displaced from the first stent, for advancement of the second stent into the body lumen. In some such embodiments, it can be that in the stent-advancement configuration, the guidewire interiorly traverses the second stent-conveyance tube segment.

In some such embodiments, it can be that when the second stent is disposed at a second target deployment location alongside the deployed first stent, a proximal-direction withdrawal of the stent-conveyance tube of the guidewire is effective to leave the stent deployed in the lumen, without further manipulation of the guidewire.

In some embodiments, an elongated stent-conveyance tube for guidewire-aided deployment of a biliary stent in a lumen of a human body comprises: a stent-conveying segment configured to have a biliary stent mounted therearound for advancement along a guidewire and into the lumen; and a guidewire-retaining segment distally displaced from the stent-conveying segment, the guidewire-retaining segment comprising (i) respective distal and proximal apertures defining a guidewire-path therethrough, and (ii) a lengthways laterally-breachable portion, wherein the laterally-breachable portion of the guidewire-retaining segment is formed to include (i) a slit portion having opposed slit-lips substantially in contact with each other and/or (ii) a perforated and/or thinned tube-wall portion.

In some embodiments, the tube is disposed within a container (e.g. sealed and/or having a sterilized interior) (e.g. a pouch) where no stent is co-disposed within the container together with the elongated stent-conveyance tube for guidewire-aided deployment.

According to embodiments disclosed herein, an elongated stent-conveyance tube for guidewire-aided deployment of a biliary stent in a lumen of a human body comprises: (a) a stent-conveying segment configured to have a biliary stent mounted therearound for advancement along a guidewire and into the lumen; and (b) a guidewire-retaining segment distally displaced from the stent-conveying segment, the guidewire-retaining segment comprising (i) respective distal and proximal apertures defining a guidewire-path therethrough, and (ii) a lengthways laterally-breachable portion, wherein the laterally-breachable portion of the guidewire-retaining segment is formed to include (i) a slit portion having opposed slit-lips substantially in contact with each other and/or (ii) a perforated and/or thinned tube-wall portion.

A method is disclosed, according to embodiments, for deploying a biliary stent in a lumen of a human body, using a guidewire arranged such that a distal end-section thereof is disposed within the body lumen and a proximal end-section thereof is outside the body. The method comprises: (a) passing the proximal end-section of the guidewire through respective distal and proximal apertures of a guidewire-retaining segment of a distal portion of a stent-conveyance tube so as to interiorly traverse the guidewire-retaining segment, the guidewire-retaining segment having a lengthways laterally-breachable portion; (b) arranging a biliary stent around a stent-conveyance tube segment that is proximally displaced from the guidewire-retaining segment; (c) distally advancing the stent-conveyance tube along the guidewire together with the stent arranged therearound, so as to deliver the stent to a target stent-deployment location within the body lumen; and (d) proximally withdrawing the stent-conveyance tube at least from the interior of the stent so as to deploy the stent in the lumen, without proximally withdrawing or distally advancing the guidewire, the proximal withdrawing of the tube being effective to cause the guidewire to laterally breach the laterally-breachable portion of the guidewire-retaining segment and thereby to decouple the guidewire from the tube.

In some embodiments, the arranging of the stent can be performed after the passing of the guidewire through the respective apertures. In some embodiments, the arranging of the stent can be performed before the passing of the guidewire through the respective apertures. In some embodiments, it can be that the arranging step is factory-performed and all other steps are performed at a medical facility.

In some embodiments, it can be that the proximal withdrawing of the tube includes applying a first proximal-withdrawal force effective to cause the guidewire to laterally breach the laterally-breachable portion of the guidewire-retaining segment, the first proximal-withdrawal force being at least 100 grams and no more than 10 kg, or at least 500 grams and no more than 5 kg, or at least 1 kg and no more than 2.5 kg, or at least 1.5 kg and no more than 2 kg. In some such embodiments, it can be that a second proximal-withdrawal force, lesser than the first proximal-withdrawal force, is effective to withdraw the stent-conveyance tube from the stent after the lateral breaching of the laterally-breachable portion of the guidewire-retaining segment by the guidewire. In some such embodiments, it can be that the arranging of the biliary stent includes engaging a locking mechanism to couple the stent to the stent-conveyance tube.

In some embodiments, the method can additionally comprise, before the proximal withdrawing of the stent-conveyance tube: disengaging the locking mechanism.

In some embodiments, a segment of the stent-conveyance tube proximally abutting the guidewire-retaining segment can have a smaller diameter than does the guidewire-retaining segment.

In some embodiments, it can be that, in the stent-advancement configuration, the guidewire does not interiorly traverse the tube segment surrounded by the stent.

In some embodiments, the stent can be deployed in the lumen without manipulating the guidewire.

In some embodiments, it can be that (i) the stent is a first stent, and the stent-conveyance tube segment is a first stent-conveyance tube segment, and (ii) the method additionally comprises: arranging a second stent to surround a second stent-conveyance tube segment that is proximally displaced from the first stent-conveyance tube segment; passing the proximal end-section of the guidewire through an aperture disposed proximally from the first stent-conveyance tube segment and distally from the second stent-conveyance tube segment, such that that the guidewire interiorly traverses the second stent-conveyance tube segment; subsequent to the proximal withdrawing of the stent-conveyance tube at least from the interior of the first stent so as to deploy the first stent in the lumen, (i) distally advancing the second stent along the stent-conveyance tube and (ii) distally advancing the stent-conveyance tube along the guidewire together with the second stent arranged therearound, so as to deliver the second stent to a second target stent-deployment location alongside the first stent; and proximally withdrawing the stent-conveyance tube and the guidewire at least from the interior of the second stent so as to deploy the second stent in the lumen, without further manipulation of the guidewire.

According to embodiments disclosed herein, a stent-deployment assembly for use with a guidewire comprises (a) a biliary stent; and (b) an elongated stent-conveyance tube comprising a guidewire-retaining segment that includes (i) respective distal and proximal apertures defining a guidewire-path therethrough, and (ii) a lengthways laterally-breachable portion, wherein: (i) in a stent-advancement configuration, (A) the guidewire passes through the respective apertures so as to interiorly traverse the guidewire-retaining segment, and (B) the stent is arranged to surround a stent-conveyance tube segment that is proximally displaced from the guidewire-retaining segment, for advancement of the stent together with the stent-conveyance tube along the guidewire into a body lumen of a human subject, and (ii) when the stent is disposed, in the stent-advancement configuration, at a target deployment location within the lumen, a proximal-direction withdrawal of the stent-conveyance tube is effective to cause the guidewire to breach the laterally-breachable portion of the guidewire-retaining segment so as to decouple the guidewire from the tube without longitudinal displacement of the guidewire.

In some embodiments, when the assembly is advanced along the guidewire in the stent-advancement configuration, the guidewire-retaining segment can be effective to retain the guidewire therewithin.

In some embodiments, it can be that in the stent-advancement configuration the guidewire does not interiorly traverse the tube segment surrounded by the stent.

In some embodiments, a segment of the stent-conveyance tube proximally abutting the guidewire-retaining segment can have a smaller diameter than does the guidewire-retaining segment.

In some embodiments, the distal aperture of the guidewire-retaining segment can face distally and the proximal aperture can face proximally.

In some embodiments, the assembly can additionally comprise a pushing tube and a proximally withdrawable locking mechanism, wherein the proximally-withdrawable locking mechanism engages the stent with the pushing tube and is effective to maintain a position of the stent relative to the tube when the assembly is advanced along the guidewire in the stent-advancement configuration.

In some embodiments, a proximal-direction withdrawal of the stent-conveyance tube can be effective to disengage the proximally-withdrawable locking mechanism.

In some embodiments, a proximal-direction withdrawal of the stent-conveyance tube effective to cause the guidewire to breach the laterally-breachable portion of the guidewire-retaining segment can be effected by applying a first proximal-withdrawal force of at least 100 grams and no more than 20 kg, or at least 500 grams and no more than 10 kg, or at least 1 kg and no more than 5 kg, or at least 1.5 kg and no more than 2.5 kg.

In some embodiments, a proximal-direction withdrawal of the stent-conveyance tube after the lateral breaching of the laterally-breachable portion of the guidewire-retaining segment by the guidewire can be effected by a second proximal-withdrawal force, lesser than the first proximal-withdrawal force. In some embodiments, the proximal-direction withdrawal of the stent-conveyance tube after the lateral breaching of the laterally-breachable portion of the guidewire-retaining segment by the guidewire can be effective to leave the stent deployed in the lumen without manipulation of the guidewire.

In some embodiments, the laterally-breachable portion of the guidewire-retaining segment can include a slit portion having opposed slit-lips either in contact with each other or displaced from each other by no more than a diameter of the guidewire.

In some embodiments, the laterally-breachable portion of the guidewire-retaining segment can include a perforated portion and/or a thinned tube-wall portion.

In some embodiments, the assembly can additionally comprise the guidewire.

In some embodiments, in the stent-advancement configuration the stent can be the only stent engaged with the guidewire.

In some embodiments, it can be that (i) the stent is a first stent, and the assembly additionally comprises a second stent, and (ii) in the stent-advancement configuration the second stent is arranged to surround a second stent-conveyance tube segment proximally displaced from the first stent, for advancement of the second stent into the body lumen.

In some embodiments, in the stent-advancement configuration the guidewire can interiorly traverse the second stent-conveyance tube segment.

In some embodiments, when the second stent is disposed at a second target deployment location alongside the deployed first stent, a proximal-direction withdrawal of the stent-conveyance tube and of the guidewire can be effective to leave the stent deployed in the lumen.

In some embodiments, the assembly can additionally comprise (i) a pushing tube disposed proximally to the second stent and configured to push the second stent off of the stent-conveyance tube, the pushing tube shaped to define a distal extension portion characterized by having a hole therein, the distal extension portion extending into a proximal end of the second stent at least as far as the hole in the proximal portion of the second stent; and (ii) a second-stent lock which prevents distal motion of the second stent past a location that is at least 1 mm proximal of a proximal end of the first stent, the second-stent lock including a locking wire engaging a distal portion of the pushing tube with the hole in the distal extension portion of the pushing tube.

According to embodiments disclosed herein, a stent-deployment assembly for use with a guidewire comprises: (a) an elongated stent-conveyance tube comprising a guidewire-retaining segment (i) having a lengthways laterally-breachable portion and (ii) configured for having the guidewire traverse therethrough; and (b) a biliary stent arranged to surround a stent-conveyance tube segment that is proximally displaced from the guidewire-retaining segment, for advancement of the stent together with the stent-conveyance tube along the guidewire into a body lumen of a human subject, wherein when the stent is disposed at a target deployment location within the lumen, a proximal-direction withdrawal of the stent-conveyance tube is effective to cause the guidewire to breach the laterally-breachable portion of the guidewire-retaining segment so as to decouple the guidewire from the tube without manipulation of the guidewire.

In some embodiments, it can be that when the assembly is advanced along the guidewire in the stent-advancement configuration, the guidewire-retaining segment is effective to retain the guidewire therewithin.

In some embodiments, it can be that in the stent-advancement configuration the guidewire does not interiorly traverse the tube segment surrounded by the stent.

In some embodiments, a segment of the stent-conveyance tube proximally abutting the guidewire-retaining segment can have a smaller diameter than does the guidewire-retaining segment.

In some embodiments, the assembly can additionally comprise a pushing tube and a proximally withdrawable locking mechanism, wherein the proximally-withdrawable locking mechanism engages the stent with the pushing tube and is effective to maintain a position of the stent relative to the tube when the assembly is advanced along the guidewire in the stent-advancement configuration.

In some embodiments, a proximal-direction withdrawal of the stent-conveyance tube can be effective to disengage the proximally-withdrawable locking mechanism.

In some embodiments, a proximal-direction withdrawal of the stent-conveyance tube can be effective to cause the guidewire to breach the laterally-breachable portion of the guidewire-retaining segment can be effected by applying a first proximal-withdrawal force of at least 100 grams and no more than 20 kg, or at least 500 grams and no more than 10 kg, or at least 1 kg and no more than 5 kg, or at least 1.5 kg and no more than 2.5 kg.

In some embodiments, a proximal-direction withdrawal of the stent-conveyance tube after the lateral breaching of the laterally-breachable portion of the guidewire-retaining segment by the guidewire can be effected by a second proximal-withdrawal force, lesser than the first proximal-withdrawal force. In some embodiments, the proximal-direction withdrawal of the stent-conveyance tube after the lateral breaching of the laterally-breachable portion of the guidewire-retaining segment by the guidewire can be effective to leave the stent deployed in the lumen without manipulation of the guidewire.

In some embodiments, the laterally-breachable portion of the guidewire-retaining segment can include a slit portion having opposed slit-lips either in contact with each other or displaced from each other by no more than a diameter of the guidewire.

In some embodiments, the laterally-breachable portion of the guidewire-retaining segment can include a perforated portion and/or a thinned tube-wall portion.

In some embodiments, the assembly can additionally comprise the guidewire.

In some embodiments, in the stent-advancement configuration the stent can be the only stent engaged with the guidewire. In some embodiments, it can be that (i) the stent is a first stent, and the assembly additionally comprises a second stent, and (ii) in the stent-advancement configuration the second stent is arranged to surround a second stent-conveyance tube segment proximally displaced from the first stent, for advancement of the second stent into the body lumen.

In some embodiments, in the stent-advancement configuration the guidewire can interiorly traverse the second stent-conveyance tube segment.

In some embodiments, when the second stent is disposed at a second target deployment location alongside the deployed first stent, a proximal-direction withdrawal of the stent-conveyance tube and of the guidewire can be effective to leave the stent deployed in the lumen.

In some embodiments, the assembly can additionally comprise (i) a pushing tube disposed proximally to the second stent and configured to push the second stent off of the stent-conveyance tube, the pushing tube shaped to define a distal extension portion characterized by having a hole therein, the distal extension portion extending into a proximal end of the second stent at least as far as the hole in the proximal portion of the second stent; and/or (2) a second-stent lock which prevents distal motion of the second stent past a location that is at least 1 mm proximal of a proximal end of the first stent, the second-stent lock including a locking wire engaging a distal portion of the pushing tube with the hole in the distal extension portion of the pushing tube.

According to embodiments of the present invention, an elongated stent-conveyance tube for guidewire-aided deployment of a biliary stent in a lumen of a human body comprises: (a) a stent-conveying segment configured to have a biliary stent mounted therearound for advancement along a guidewire and into the lumen; and (b) a guidewire-retaining segment distally displaced from the stent-conveying segment, the guidewire-retaining segment comprising (i) respective distal and proximal apertures defining a guidewire-path therethrough, and (ii) a lengthways laterally-breachable portion, wherein the laterally-breachable portion of the guidewire-retaining segment is formed to include (i) a slit portion having opposed slit-lips substantially in contact with each other and/or (ii) a perforated tube-wall portion and/or (iii) a thinned tube-wall portion.

A method is disclosed, according to embodiments of the present invention, for deploying a biliary stent in a lumen of a human body, using a guidewire arranged such that a distal end-section thereof is disposed within the body lumen and a proximal end-section thereof is outside the body. The method comprises: (a) passing the proximal end-section of the guidewire through respective distal and proximal apertures of a guidewire-retaining segment of a distal portion of a stent-conveyance tube so as to interiorly traverse the guidewire-retaining segment, the guidewire-retaining segment having a lengthways laterally-breachable portion; (b) arranging a biliary stent around a stent-conveyance tube segment that is proximally displaced from the guidewire-retaining segment; (c) distally advancing the stent-conveyance tube along the guidewire together with the stent arranged therearound, so as to deliver the stent to a target stent-deployment location within the body lumen; and (d) proximally withdrawing the stent-conveyance tube at least from the interior of the stent so as to deploy the stent in the lumen, without proximally withdrawing or distally advancing the guidewire, the proximally withdrawing of the tube being effective to cause the guidewire to laterally breach the laterally-breachable portion of the guidewire-retaining segment and thereby to decouple the guidewire from the tube.

In some embodiments, the arranging of the stent can be performed after the passing of the guidewire through the respective apertures. In some embodiments, arranging of the stent can be performed before the passing of the guidewire through the respective apertures. In some embodiments, the arranging step can be factory-performed and all other steps can be performed at a medical facility.

In some embodiments, the proximal withdrawing of the stent-conveyance tube can include applying a first proximal-withdrawal force effective to cause the guidewire to laterally breach the laterally-breachable portion of the guidewire-retaining segment, the first proximal-withdrawal force being at least 100 grams and no more than 10 kg, or at least 500 grams and no more than 5 kg, or at least 1 kg and no more than 2.5 kg, or at least 1.5 kg and no more than 2 kg. In some embodiments, the proximal withdrawing of the stent-conveyance tube can include applying a second proximal-withdrawal force, lesser than the first proximal-withdrawal force, to withdraw the stent-conveyance tube from the stent after the lateral breaching of the laterally-breachable portion of the guidewire-retaining segment by the guidewire.

In some embodiments, the arranging of the biliary stent can include engaging a proximally withdrawable locking mechanism to couple the stent to a pushing tube disposed to surround a portion of the stent-conveyance tube that is proximal to the stent. In some embodiments, proximally withdrawing the stent-conveyance tube can disengage the proximally-withdrawable locking mechanism.

In some embodiments, a segment of the stent-conveyance tube proximally abutting the guidewire-retaining segment can have a smaller diameter than does the guidewire-retaining segment.

In some embodiments, it can be that in the stent-advancement configuration the guidewire does not interiorly traverse the stent-conveyance-tube segment surrounded by the stent.

In some embodiments, the stent can be deployed in the lumen without manipulating the guidewire.

In some embodiments, it can be that (i) the stent is a first stent, and the stent-conveyance-tube segment is a first stent-conveyance-tube segment, and (ii) the method additionally comprises: (a) arranging a second stent to surround a second stent-conveyance-tube segment that is proximally displaced from the first stent-conveyance-tube segment; (b) passing the proximal end-section of the guidewire through an aperture disposed proximally from the first stent-conveyance-tube segment and distally from the second stent-conveyance-tube segment, such that the guidewire interiorly traverses the second stent-conveyance-tube segment; (c) subsequent to the proximal withdrawing of the stent-conveyance tube at least from the interior of the first stent so as to deploy the first stent in the lumen, (i) distally advancing the second stent along the stent-conveyance tube and (ii) distally advancing the stent-conveyance tube along the guidewire together with the second stent arranged therearound, so as to deliver the second stent to a second target stent-deployment location alongside the first stent; and (d) proximally withdrawing the stent-conveyance tube and the guidewire at least from the interior of the second stent so as to deploy the second stent in the lumen.

In some embodiments, the method can additionally comprise: (i) arranging a pushing tube proximally to the second stent, the pushing tube shaped to define a distal extension portion characterized by having a hole therein, the distal extension portion extending into a proximal end of the second stent at least as far as the hole in the proximal portion of the second stent, and (b) engaging a second-stent lock to prevent distal motion of the second stent past a location that is at least 1 mm proximal of a proximal end of the first stent, the second-stent lock including a locking wire engaging a distal portion of the pushing tube with the hole in the distal extension portion of the pushing tube. In some embodiments, the deploying of the second stent in the lumen can include using the pushing tube to push the second stent off of the stent-conveyance tube.

A method is disclosed, according to embodiments of the present invention, for deploying a biliary stent in a lumen of a human body, using a guidewire arranged such that a distal end-section thereof is disposed within the body lumen and a proximal end-section thereof is outside the body. The method comprises: (a) providing a stent-deployment assembly comprising: (i) a biliary stent; and (ii) an elongated stent-conveyance tube comprising a guidewire-retaining segment that includes (i) respective distal and proximal apertures defining a guidewire-path therethrough, and (ii) a lengthways laterally-breachable portion; (b) distally advancing the stent-deployment assembly along the guidewire into a body lumen of a human subject in a stent-advancement configuration in which (i) the guidewire passes through the respective apertures so as to interiorly traverse the guidewire-retaining segment, and (ii) the stent is arranged to surround a stent-conveyance tube segment that is proximally displaced from the guidewire-retaining segment; and (c) when the stent is disposed, in the stent-advancement configuration, at a target deployment location within the lumen, withdrawing the stent-conveyance tube a proximal-direction so as to cause the guidewire to breach the laterally-breachable portion of the guidewire-retaining segment and decouple the guidewire from the tube without longitudinal displacement of the guidewire.

In some embodiments, the proximal withdrawing of the stent-conveyance tube can include applying a first proximal-withdrawal force effective to cause the guidewire to laterally breach the laterally-breachable portion of the guidewire-retaining segment, the first proximal-withdrawal force being at least 100 grams and no more than 10 kg, or at least 500 grams and no more than 5 kg, or at least 1 kg and no more than 2.5 kg, or at least 1.5 kg and no more than 2 kg. In some embodiments, the proximal withdrawing of the stent-conveyance tube can include applying a second proximal-withdrawal force, lesser than the first proximal-withdrawal force, to withdraw the stent-conveyance tube from the stent after the lateral breaching of the laterally-breachable portion of the guidewire-retaining segment by the guidewire.

In some embodiments, it can be that (i) the stent-deployment assembly additionally comprises a pushing tube and a proximally withdrawable locking mechanism, and (ii) the proximally withdrawable locking mechanism engages the stent with the pushing tube and is effective to maintain a position of the stent relative to the tube when the assembly is advanced along the guidewire in the stent-advancement configuration. In some embodiments, proximally withdrawing the stent-conveyance tube can disengage the proximally-withdrawable locking mechanism.

In some embodiments, a segment of the stent-conveyance tube proximally abutting the guidewire-retaining segment can have a smaller diameter than does the guidewire-retaining segment. In some embodiments, it can be that in the stent-advancement configuration the guidewire does not interiorly traverse the stent-conveyance-tube segment surrounded by the stent.

In some embodiments, the stent can be deployed in the lumen without manipulating the guidewire.

In some embodiments, it can be that (i) the stent is a first stent, the stent-conveyance-tube segment is a first stent-conveyance-tube segment, (ii) the assembly additionally comprises (A) a pushing tube disposed proximally to the second stent and shaped to define a distal extension portion characterized by having a hole therein, the distal extension portion extending into a proximal end of the second stent at least as far as the hole in the proximal portion of the second stent; and (B) a second-stent lock which prevents distal motion of the second stent past a location that is at least 1 mm proximal of a proximal end of the first stent, the second-stent lock including a locking wire engaging a distal portion of the pushing tube with the hole in the distal extension portion of the pushing tube, and (iii) the method additionally comprises: (a) arranging a second stent to surround a second stent-conveyance-tube segment that is proximally displaced from the first stent-conveyance-tube segment; (b) subsequent to the proximal withdrawing of the stent-conveyance tube at least from the interior of the first stent so as to deploy the first stent in the lumen, (i) distally advancing the second stent along the stent-conveyance tube and (ii) distally advancing the stent-conveyance tube along the guidewire together with the second stent arranged therearound, so as to deliver the second stent to a second target stent-deployment location alongside the first stent; and (c) proximally withdrawing the stent-conveyance tube and the guidewire at least from the interior of the second stent so as to deploy the second stent in the lumen. In some embodiments, the deploying of the second stent in the lumen can include using the pushing tube to push the second stent off of the stent-conveyance tube.

According to embodiments of the present invention, a stent-deployment assembly for use with a guidewire, comprises: (a) an elongated stent-conveyance tube comprising a guidewire-retaining segment configured for having the guidewire traverse therethrough; (b) a biliary stent arranged to surround a first stent-conveyance-tube segment that is proximally displaced from the guidewire-retaining segment, for advancement of the stent together with the stent-conveyance tube along the guidewire into a body lumen of a human subject; (c) a pushing tube arranged to surround the stent-conveyance tube, proximal to the stent; and (d) a proximally-withdrawable locking mechanism arranged to engage the stent with the pushing tube, wherein: (i) the locking mechanism is effective to maintain a position of the stent relative to the stent-conveyance tube when the stent-deployment assembly is advanced along the guidewire, and (ii) a proximal withdrawal of the stent-conveyance tube is effective to disengage the proximally withdrawable locking mechanism.

In some embodiments, the proximally withdrawable locking mechanism can include a first member engaged with the elongated stent-conveyance tube. In some embodiments, the proximally withdrawable locking mechanism can include a second member arranged to transversely pass through a portion of the pushing tube.

BRIEF DESCRIPTION OF THE DRAWINGS

The invention will now be described further, by way of example, with reference to the accompanying drawings, in which the dimensions of components and features shown in the figures are chosen for convenience and clarity of presentation and not necessarily to scale. In the drawings.

DETAILED DESCRIPTION OF EMBODIMENTS

Figure 1:
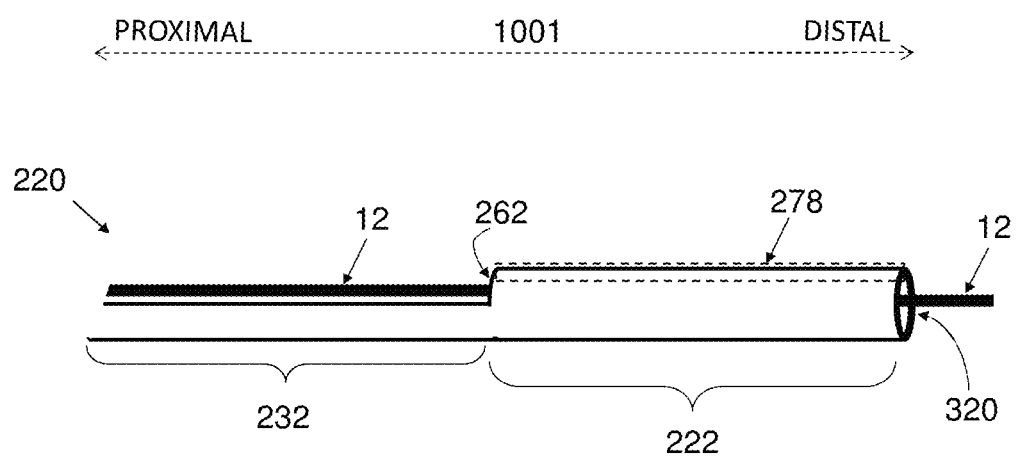
FIG. 1 is a schematic illustration of a distal portion of a stent-conveyance tube, shown engaged with a guidewire, in accordance with embodiments of the present invention.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are generally used to designate like elements.

According to embodiments, a stent assembly includes a biliary stent mounted on a catheter tube adapted for conveying the stent to a target deployment location within a lumen of a human subject, for example, to maintain flow viability of a bile duct. The assembly is configured for advancement along a guidewire which is typically inserted into the subject's body in advance of deploying the stent. A distal end of the guidewire is disposed within the target lumen, and the proximal end remains outside the body. In the case of employing short-wire systems, the guidewire can be externally locked. The terms 'distal' and 'proximal' are used throughout this disclosure and the appended claims as follows: 'distal' means further into the body (along an insertion path) from a point of entry into the body, while 'proximal' means closer to the point of entry into the body. Where the terms are used in reference to apparatus outside of a patient's body, a distal portion or distal end is that portion or end of the apparatus configured to be inserted into the body first, while a proximal end or proximal portion is either inserted last or may never be inserted (as in the case of a guidewire, for example). Additionally, when used relatively, e.g. 'distally displaced from' or 'proximal of', the meaning is, respectively, closer to the distal end than' or 'closer to the proximal end than'.

As will be further described hereinbelow and in the accompanying figures, a catheter tube (alternatively called, equivalently, 'guide tube,' 'stent-conveyance tube,' or, simply, 'tube') for conveyance of the stent is disclosed as having, at or near a distal tip, arrangements for engaging a guidewire. Apertures are provided on either end of a longitudinal guidewire-engaging or guidewire-retaining segment of the tube, and the guidewire can be threaded through these apertures so as to traverse the interior of the guidewire-retaining segment of the tube. The guidewire does not interiorly traverse the tube segment proximal to the guidewire-retaining segment, and thus 'leaves' the interior of the tube, at least temporarily, at the proximal aperture. The distal aperture can be at the distal tip of the tube, or it can be displaced proximally from the tip. It is preferable that the distal aperture faces distally, i.e., faces in a direction in which the distal tip is facing, within 15° of that direction, or within 30° of that direction, or within 45° of that direction. The proximal aperture preferably faces proximally, i.e., faces in a direction opposite to the direction in which the distal tip is facing, or within 15° of that 'opposite' direction, or within 30° or within 45° of that 'opposite' direction. Thus, when the guidewire exits the proximal aperture, it is directed to continue alongside the tube (and alongside the stent that surrounds the tube) proximal to the proximal aperture.

With the guidewire passing through the interior of the guidewire-retaining segment, the tube can be advanced along the length of the guidewire with little resistance from the guidewire, for example pushed forward by an additional stent engaged with the guidewire or by a 'pusher' catheter engaged with the guidewire. The stent can be mounted on the tube before or after the tube is engaged with the guidewire, so as to surround a segment of the tube that is proximal to the guidewire-retaining segment. There can be a gap between the guidewire-retaining segment and the stent-carrying segment.

The configuration in which the stent is mounted on the tube so as to surround a segment that is proximal to the guidewire-retaining segment, and in which the tube is engaged with the guidewire in that the guidewire passes through the interior of the guidewire-retaining segment, is referred to herein as the 'stent-advancement configuration' of the stent assembly.

The guidewire-retaining segment is configured to retain the guidewire therewithin during the advancement of the stent into the body lumen in the stent-advancement configuration. In some embodiments, the relative longitudinal stability of the position of the stent relative to the tube is accomplished using a locking stent as will be discussed hereinbelow. The guidewire-retaining segment has a lengthways, laterally breachable portion, making the guidewire-retaining segment laterally breachable by the guidewire. The guidewire-retaining segment of the tube is designed to be laterally breached by the guidewire when a shearing force is applied, beginning at the proximal aperture when the tube is proximally withdrawn once the stent is deployed and anchored in the lumen (and any locking system is 'unlocked'). The laterally-breachable portion can be a weakened or pre-breached sidewall of the guidewire-retaining portion, as will be discussed in greater detail hereinbelow with respect to FIGS. 1 and 2A-2B.

Once the stent has been advanced to a target stent-deployment location in the lumen of the patient's body, e.g., the bile duct, the stent-conveyance tube can be withdrawn proximally so as to leave the stent deployed in the lumen. The stent is preferably self-anchoring with one or more anchor flaps maintaining the position of the stent against the force used to withdraw the tube, such that the stent slides off the distal end of the tube. Once the proximal aperture of the guidewire-retaining reaches the edge of the stent, the guidewire exiting the proximal aperture is trapped against the proximal aperture by the unmoving stent, and the resulting shearing force causes the guidewire to breach the laterally-breachable portion of the guidewire-retaining segment. Continued application of the force causes the guidewire to laterally exit the breached guidewire-retaining segment and thus be disengaged or decoupled therefrom. The force necessary to breach the laterally-breachable portion of the guidewire-retaining segment can be at least 100 grams and no more than 20 kg. In various embodiments, the necessary force can be at least 500 grams and no more than 10 kg, or at least 1 kg and no more than 5 kg, or at least 1.5 kg and no more than 2.5 kg. Once the guidewire-retaining portion is completely breached, the force necessary to withdraw the tube from the anchored stent can be less than the force required to breach the guidewire-retaining portion.

We now refer to the figures, and in particular to FIG. 1, which shows a schematic illustration of a distal portion of a stent-conveyance tube 220 according to a non-limiting example. The tube 220 is elongated in that it is many times (e.g., 100 or 200 or more) times longer than it is thick. The tube 220 is shown as engaged with the distal end of a guidewire 12 for purposes of illustrating some of the features of the tube 220 and the manner in which it engages with the guidewire 12. Distal and proximal directions with respect to the tube and stent are shown by means of arrow 1001.

As shown in FIG. 1, a first distal segment 222 is demarcated by a distal aperture 320 and a proximal aperture 262. In some embodiments, the distal aperture is not necessarily at the distal tip (the tip of the distal portion of the tube 220) but rather is displaced proximally therefrom. In such embodiments, the distal aperture 320 preferably faces distally, or within 15° or 30° or 45° of the distal direction. Similarly, the proximal aperture 262 preferably faces proximally, as shown in FIG. 1, or within 15° or 30° or 45° of the proximal direction. A main purpose of the engagement of the tube 220 with the guidewire 12 is to enable distal advancement of the tube, along with one or more stents conveyed by the tube 220, to a target stent-deployment location within a lumen of a subject's body; therefore it can be desirable for the guidewire-engaged segment of the tube (with the guidewire engaged within) to traverse the length of the guidewire with a minimum of resistance, and a suitable angling of the apertures 320, 262 can contribute to the lowering of resistance from frictional and other forces. The guidewire-engaged segment 222 is also called a guidewire-retaining segment in this disclosure because the segment is designed to retain the guidewire therewithin as the tube traverses the guidewire. The guidewire-retaining segment 222 includes a lengthways laterally-breachable portion 278 which is configured to enable the retained guidewire 12 to breach the guidewire-retaining segment 222 laterally when a suitable shearing force is applied, as will be discussed in further detail hereinbelow.

It can be seen in FIG. 1 that a segment 232 proximal to the guidewire-retaining segment 222 has a diameter less than that of the guidewire-retaining segment, and it can be readily understood that the difference in diameters enables use of a straightforward design for the proximal aperture 262, i.e., formed as to face proximally as in the FIG. 1 example. In other examples of a stent-conveyance tube 222 according to embodiments (not illustrated), the diameter of proximal segment 232 can be the same as or greater than the diameter of guidewire-retaining segment 222, and the proximal aperture 262 can be positioned and angled accordingly. In any case, after exiting the guidewire-retaining segment 222 via the proximal aperture, the guidewire 12 extends proximally outside the tube 222 and does not interiorly traverse the next segment 232.

Figure 2A:
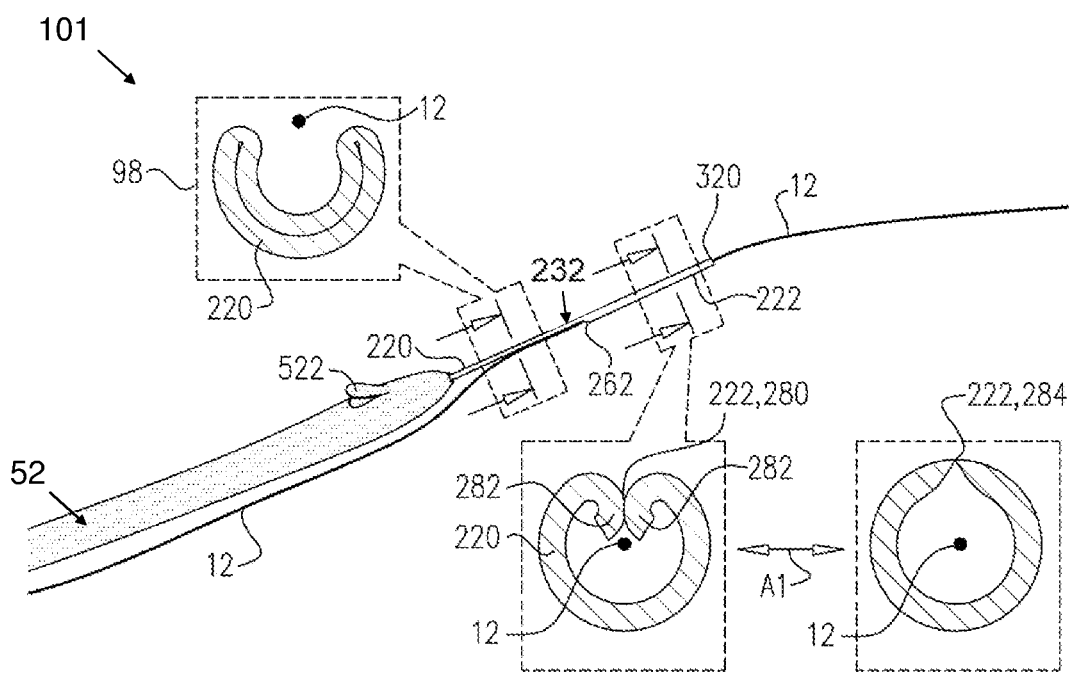
FIGS. 2A and 2B are schematic illustrations of a stent assembly and its deployment in a lumen of a human subject, in accordance with embodiments of the present invention.
Figure 2B:
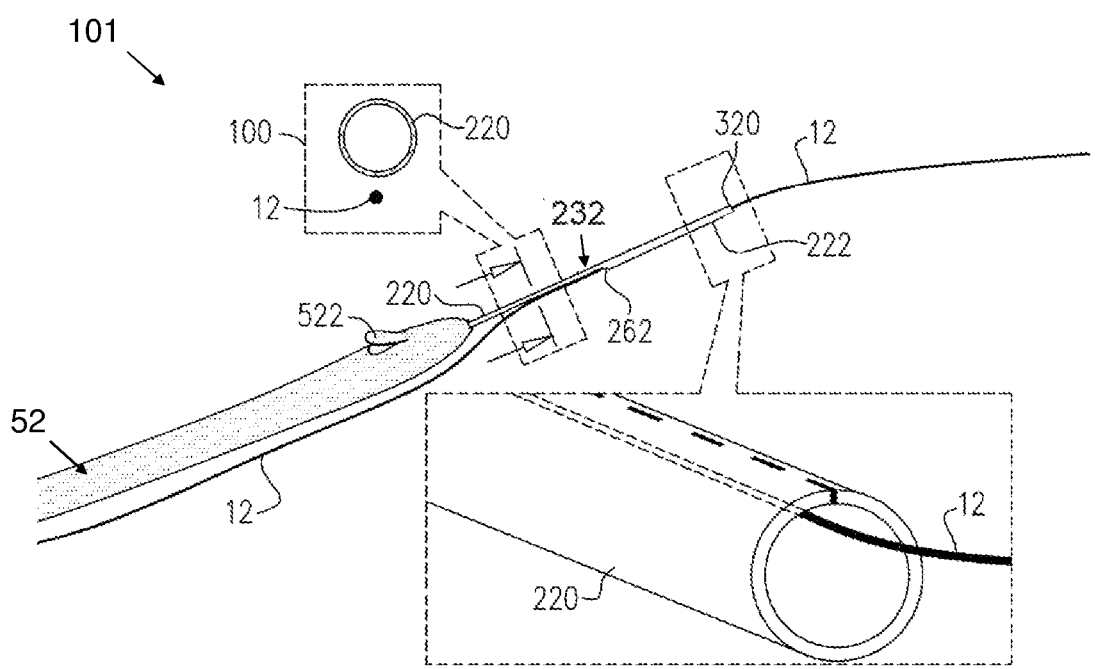

Referring now to FIGS. 2A and 2B, examples of configuring the distal end of a stent assembly 101 are illustrated schematically. The stent assembly 101 includes the stent-conveyance tube 220 of FIG. 1 together with a biliary stent 52 mounted on the tube 220 so as to surround a segment of the tube 220. In some embodiments, the stent assembly additionally includes the guidewire 12. The stent 52 is displaced proximally from the guidewire-retaining segment 222, and is not necessarily contiguous to the guidewire-retaining segment 222, i.e., in the example shown there is an intervening segment 232 as was shown in FIG. 1. As shown in FIGS. 2A and 2B, the guidewire 12 extends proximally outside of the tube 220 after exiting the proximal aperture 262 and continues proximally alongside the stent 52.

The differences between the examples of FIG. 2A and FIG. 2B are to be found in the specific cross-section design of segment 232 (and of more proximal segments of the tube 220), and in the specific design of the laterally-breachable portion 278.

With respect to the cross-section of segment 232, in the example shown in FIG. 2A, the cross-section of the tube 220 at segment 232 (as shown in Detail Box 98) is open and U-shaped. In other words, proximal to the guidewire-retaining segment 222, the tube need not be a complete cylinder. The respective section of the tube can be formed with a open U-shape, or can be a collapsed or crushed segment of a completely cylindrical segment. Use of the U-shape can be helpful in some designs for facilitating the routing of guidewire 12 as it exits the proximal aperture 262. In contrast to the U-shape example of FIG. 2A, the cross-section of the tube 220 at segment 232 is a complete circle in the example shown in FIG. 2B, i.e., the tube 220 is shaped as a complete cylinder in segment 232. The segment of the tube 220 surrounded by the stent 52 can likewise employ either cross-section, and can simply continue the design choice of intermediating segment 232. Neither segment is limited to the specific designs illustrated in the non-limiting examples of FIGS. 2A and 2B, and any cross-sectional design can be employed.

Figure 2C:
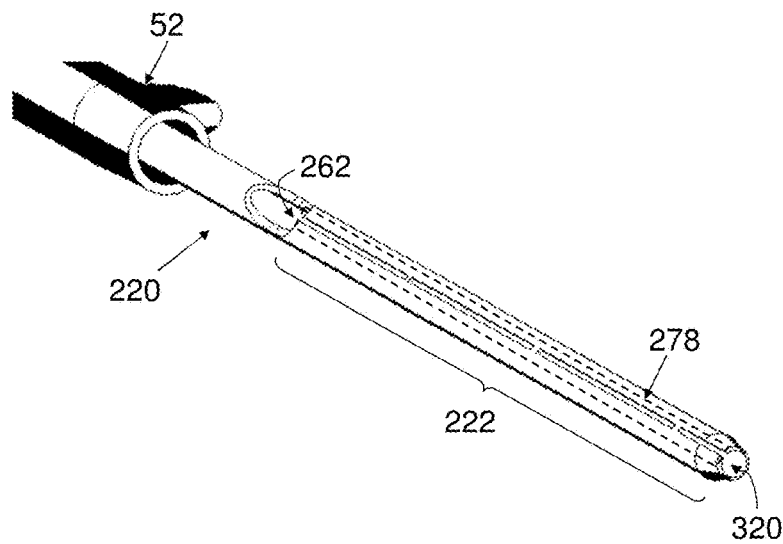
FIG. 2C is a perspective view of a distal portion of a stent-conveyance tube in accordance to embodiments of the present invention.

With respect to the design of the laterally breachable portion 278 of the guidewire-retaining segment 232, the first of the two cross-sectional detail boxes labeled A1 in FIG. 2A shows that the laterally breachable portion 278 can include a slit 280 shaped to define two 'lips' 282 ('slit lips') that are in contact with each other, or nearly in contact with each other but not farther apart than the diameter of the guidewire 12, to define a closed-slit configuration in the absence of any forces applied to slit lips 282. The slit lips 282, are displaceable from each other, typically by suitable application of a force to cause the displacement, to define an opened-slit configuration. The second of the two cross-sectional detail boxes labeled A1 in FIG. 2A shows that the laterally breachable portion 278 can include a weakened sidewall portion 284, which is splittable/breachable by the guidewire 12 in response to a suitably applied force. A third example of a design of the laterally breachable portion 278 is shown in the detail box in FIG. 2B, in which the laterally breachable portion 278 is shown to be perforated, and thus splittable/breachable by the guidewire 12 in response to a suitably applied force. FIG. 2C shows the distal tip of a stent-conveyance tube 220 according to embodiments. The design of FIG. 2C includes a laterally breachable portion 278 embodied as a perforated portion of the guidewire-retaining segment 222 and thus is conceptually similar to the design illustrated in FIG. 2B.

Design of the laterally breachable portion 278 is not limited to the specific designs illustrated in the non-limiting examples of FIGS. 2A and 2B, and any functionally equivalent design that suitably enables the lateral breaching of the guidewire-retaining segment 222 can be used.

One or more anchor flaps 522 are formed on the external surface of the stent 52, as shown in FIGS. 2A-2B, so that when the stent 52 is deployed at a target location within a lumen of the subject, the one or more anchor flaps are effective to anchor the stent in place by catching or snagging on the interior wall of the lumen.

Figure 3:
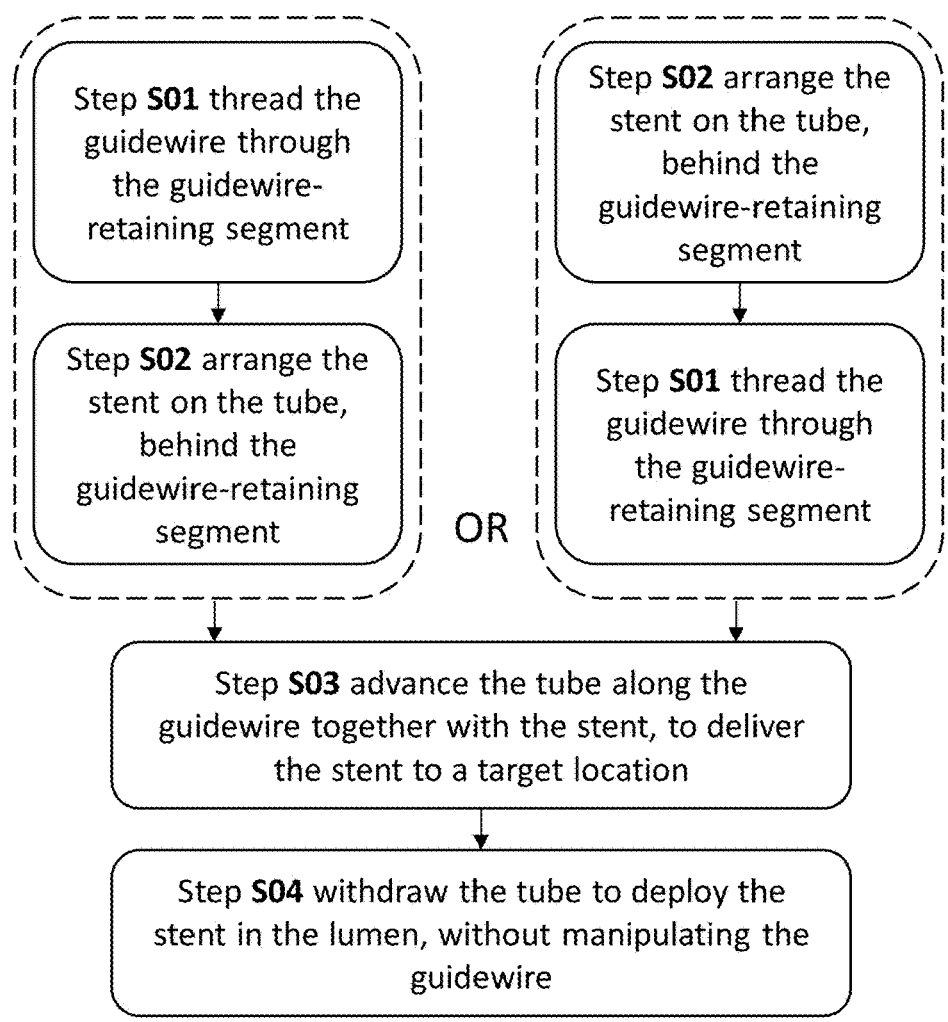
FIG. 3 shows a flowchart of a method for deploying a biliary stent in a lumen of a human subject, in accordance with embodiments of the present invention.

Referring now to FIG. 3, a method is disclosed for deploying a biliary stent in a lumen of a human body. As illustrated by the flow chart in FIG. 3, the method comprises:

Step S01 passing an end, e.g., a proximal end, of the guidewire 12 through the guidewire-retaining segment 222 of the stent-conveyance tube 220 via respective distal and proximal apertures 320, 262; and Step S02 arranging the stent 52 on the stent-conveyance tube 220, proximal to the guidewire-retaining segment 222. As mentioned earlier, there can be an additional segment 232 intermediating between the guidewire-retaining segment 222 and the tube segment on which stent 52 is mounted.

As shown in the flowchart, Steps S01 and S02 can be carried out in either order, i.e., first Step S01 and then Step S02, or first Step S02 and then Step S01. As an example, it may be desirable to have the tube 220 engaged with the guidewire 12 before mounting the stent 52 on the tube 220. As another example, it may be desirable to have the stent 52 in place on the tube 220 before engaging the tube 220 with the guidewire 12.

After carrying out Steps S01 and S02, the stent assembly 101 can be seen to be in a 'stent-advancement configuration' in which the guidewire 12 passes through the distal and proximal apertures 320, 262 so as to interiorly traverse the guidewire-retaining segment 222, and the stent 52 is arranged to surround a stent-conveyance tube segment that is proximally displaced from the guidewire-retaining segment 222, for advancement of the stent 52 together with the stent-conveyance tube 220 along the guidewire 12 into a body lumen of a human subject.

The method additionally comprises:

Step S03 advancing the stent-conveyance tube 220 along the guidewire 12 together with the stent 12, i.e., with guidewire-retaining segment 222 engaged with the guidewire 12, to deliver the stent 52 to a target location in a lumen, e.g., a bile duct, of a patient; and Step S04 proximally withdrawing the stent-conveyance tube 220 to deploy the stent in the lumen, without manipulating the guidewire. The term 'without manipulating the guidewire' describes a situation wherein the stent 52 is anchored in the lumen by one or more anchor flaps 522 and is substantially immobilized (e.g., won't move longitudinally more than 1 mm, or more than 2 mm, or more than 3 mm, or more than 5 mm, or more than 10 mm) so as to resist longitudinal forces associated with withdrawing the stent-conveyance tube 220.

Steps of the instant method for deploying a biliary stent in a lumen of a human body using a stent assembly 101, according to embodiments of the present invention, will be explained in greater detail in connection with FIGS. 4A-C.

Figure 4A:
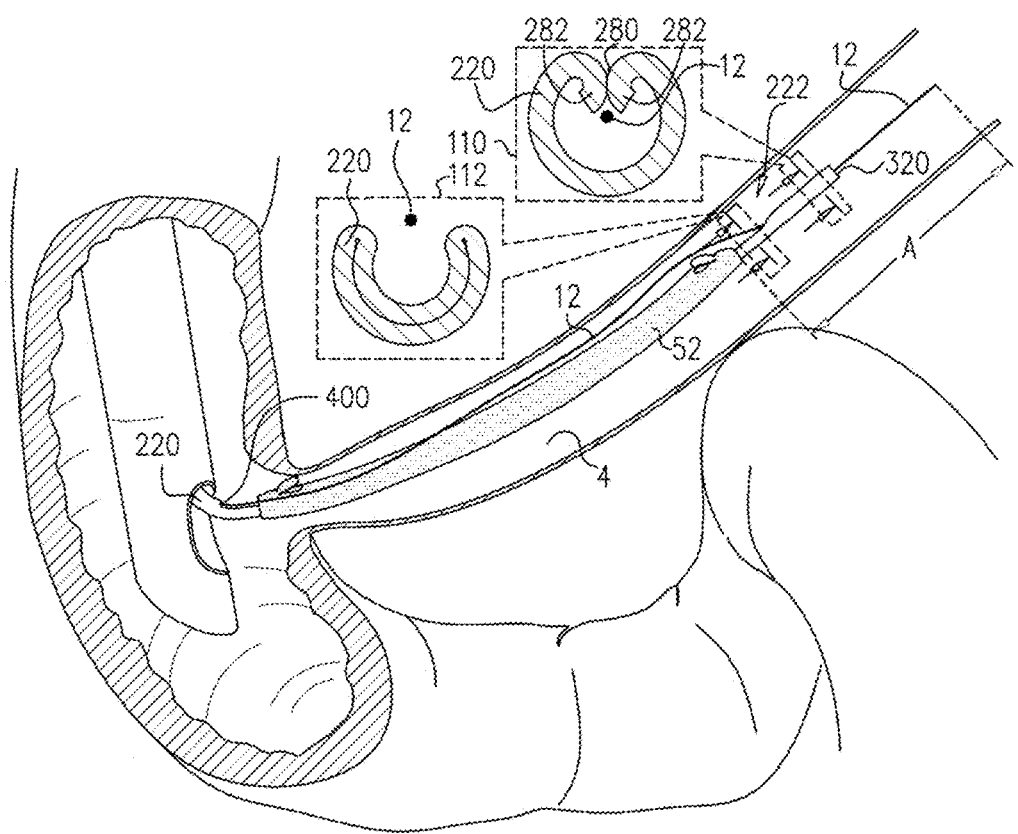
FIGS. 4A, 4B and 4D are schematic illustrations depicting a general overview of a method for deploying a stent in a lumen of a subject, in accordance with embodiments of the present invention.

FIG. 4A shows, schematically, a stent assembly 101 such as any one the stent assembly 101 of FIGS. 2A-2B upon 'arrival' of the stent 52 at a target location, with the stent assembly 101 still in the 'stent-advancement configuration' as described hereinabove, in a lumen 4 of a patient. In terms of the method steps described in the preceding paragraphs, FIGS. 2A-2B are 'snapshots' of a stent assembly 101 after carrying out Steps S01 and S02, and FIG. 4A is a snapshot after carrying out Step S03.

In the particular example of the stent assembly 101 illustrated in FIG. 4A the tube segment 232 proximal to the guidewire-retaining segment 222 has the 'crushed U-shape' cross-section shown in FIG. 2A, and uses the slit 280/'slit-lips' 282 design option for the laterally breachable portion 278 of the guidewire-retaining segment 222, as also shown in FIG. 2A. Selection of this design example throughout FIGS. 4A-4B is for convenience only, and any of the design options of FIGS. 2A-2B, or their functional equivalents, can be employed to equal benefit.

Unlike the illustrations of FIGS. 2A-2B, FIG. 4A shows the proximal end of the stent 52, and shows the guidewire 12 re-entering the interior of the tube stent-conveyance tube 220 through aperture 400. While this configuration is optional, it can be desirable to re-engage the guidewire 12 behind (i.e., proximal to) the stent 52 in the stent-advancement configuration. As a non-limiting example, this configuration can simplify control of the guidewire and stent-conveyance tube both during stent advancement and during later withdrawal of the tube and/or guidewire. The passage of the guidewire 12 also restricts the ability of the stent 52 to slip proximally with respect to the tube 220 during the stent advancement step S03. In addition, as will be discussed hereinbelow, using the configuration can be advantageous if it is desired to deliver a second stent together with (i.e., immediately or soon after, and alongside) delivery of the 'first' stent.

Figure 4B:
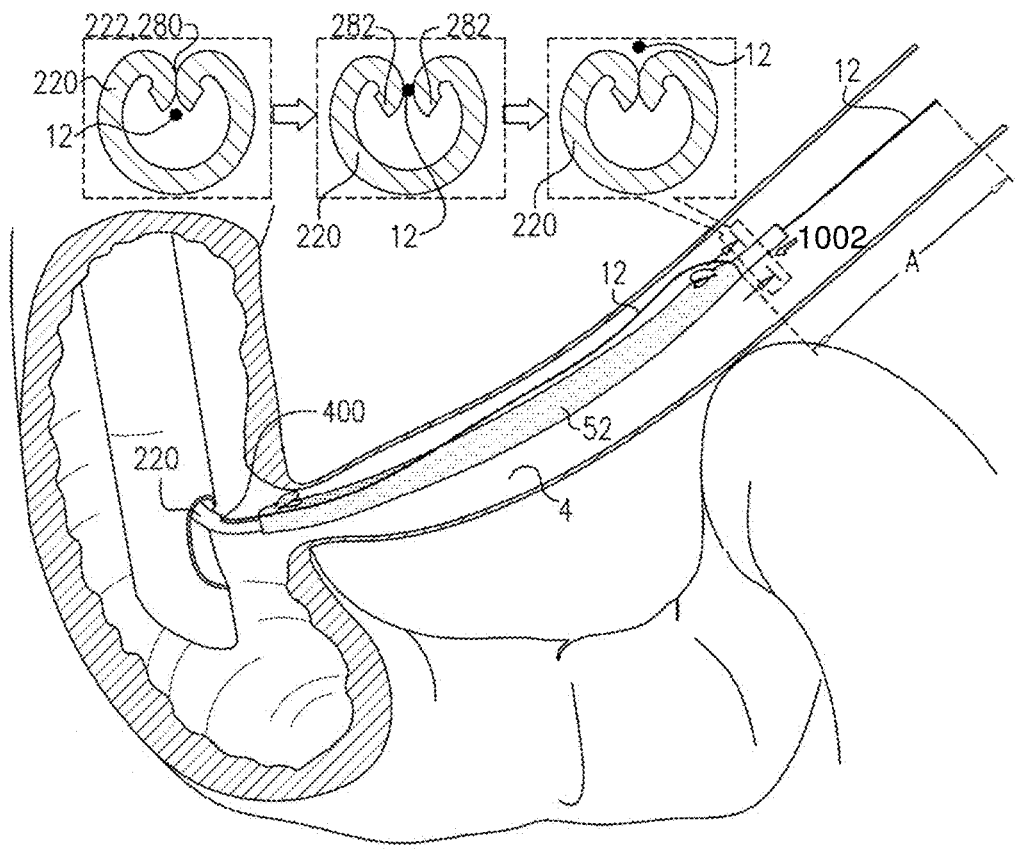
Figure 4C:
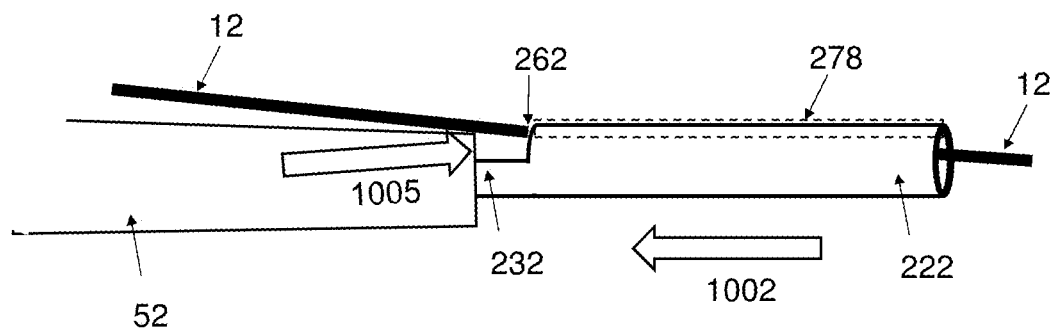
FIG. 4C is a schematic illustration of a distal portion of a stent-conveyance tube, shown engaged with a guidewire, during proximal withdrawal of a stent-conveyance tube, in accordance with embodiments of the present invention.

We now refer to FIGS. 4B and 4C, which schematically illustrate the dynamic of Step S04. Step S04 preferably is carried out after the stent assembly 101 has been advanced along the guidewire 12 until the stent 52 is at a target location, for example, one that may have been selected in advance, or one that may have been selected by using an endoscope inserted along guidewire 12 or another guidewire. In Step S04, the stent-conveyance tube 220 is withdrawn proximally, i.e., in the direction of arrow 1002 of FIGS. 4B and 4C. The stent 52, as noted hereinabove, is configured to be anchored in a wall of lumen 4 by anchor flap 522, or at least prevented from proximal travel of more than 1 mm, of more than 2 mm, of more than 3 mm, or more than 5 mm. As indicated in FIG. 4C, the travel of the stent-conveyance tube 220 in the proximal direction causes aperture 262, through which the guidewire 12 exits the guidewire-retaining segment 222, to approach the distal end of stent 52. This approaching causes a shearing force (schematically represented by arrow 1005) to impinge upon the portion of the guidewire 12 proximal to aperture 262 and eventually of the portion of the guidewire 12 distal to aperture 262. When the force applied in order to proximally withdraw the stent-conveyance tube 220 is in a suitable range, or alternatively/equivalently above a minimally necessary level of force, the shearing force starting at aperture 262 causes the guidewire 12 to breach the laterally-breachable portion 278 of the guidewire-retaining segment 222. Suitable ranges of force to be applied to proximally withdraw the tube 220 so as to breach the laterally-breachable portion 278 include: at least 100 grams and no more than 20 kg, or at least 500 grams and no more than 10 kg, or at least 1 kg and no more than 5 kg, or at least 1.5 kg and no more than 2.5 kg. Once the sidewall of the tube 220 in the guidewire-retaining segment 222, i.e., the laterally breachable portion, is breached, the guidewire 12 exits the guidewire-retaining segment 222 laterally and thus decouples or disengages from the tube 220. The breaching is shown in the three cross-sectional detail boxes of FIG. 4B, each representing a point in time, as follows: in the leftmost detail box, the guidewire 12 is still in the interior of the guidewire-retaining segment 222; in the center detail box, the guidewire 12 can be seen actively breaching the laterally-breachable portion; and in the rightmost detail box, the guidewire 12 can be seen to be outside of the guidewire-retaining segment 222 having exited laterally therefrom.

Figure 4D:
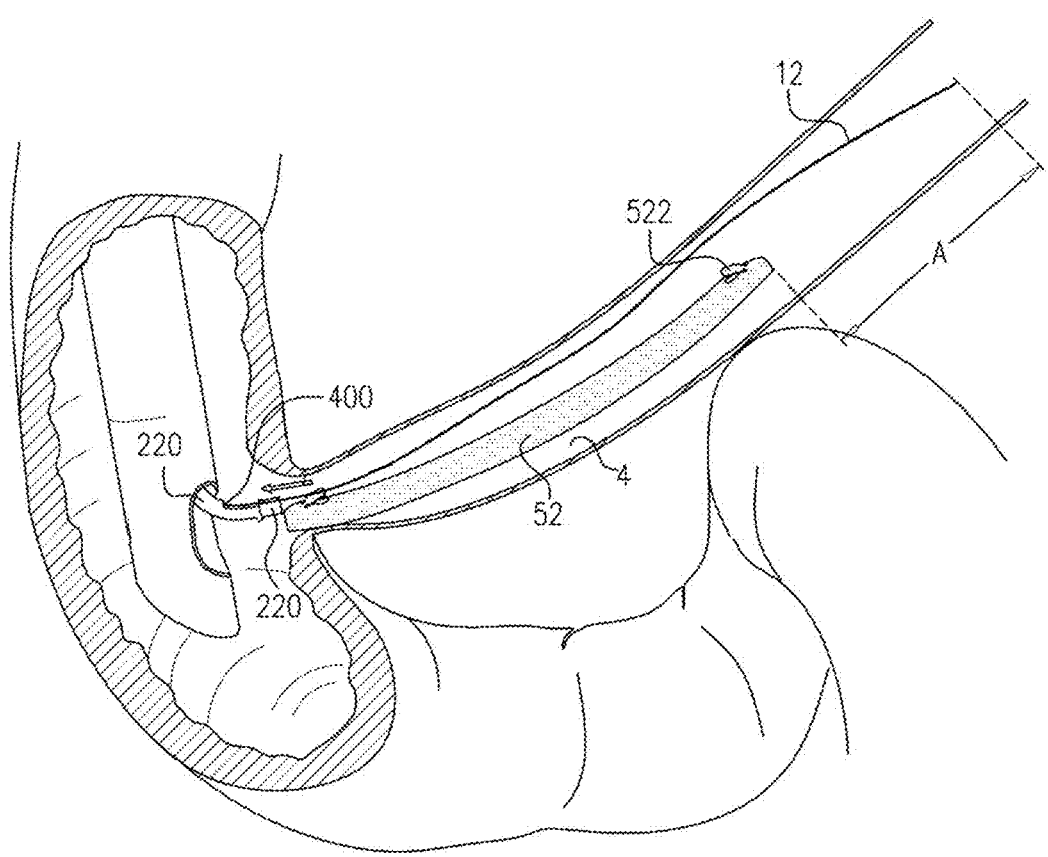

Thus, in FIG. 4D, it can be seen that the stent-conveyance tube 220 has been pulled back proximally at least to the extent that its distal tip is no longer distally displaced from the distal end of the stent 52, and the stent 52 is deployed in the lumen 4. It should be noted that the force required to continue withdrawing the stent-conveyance tube 220 after disengagement from the guidewire 12 can be of lesser magnitude than force required for breaching the laterally-breachable portion 278 of the guidewire-retaining segment 222. The deployment of the stent 52 in the lumen 4 using the disclosed method and stent assembly 101 can be carried out without manipulating the guidewire 12 to 'release' or disengage the tube therefrom. In particular, there is no need for causing distal or proximal movement of the guidewire 12 in order to carry out the method. Some inadvertent movement of the guidewire 12 may occur during or after Step 04, for example from incidental contact or friction with the withdrawing tube 220, although such movement is not substantive and does not impinge upon the scope of the invention which excludes necessitating any directed movement or manipulation of the guidewire 12.

In some embodiments, the guidewire 12 can be left in place for use with other surgical and diagnostics instruments and tools.

In some embodiments, when the stent 52 is advanced, together with the stent-conveyance tube 220, along the guidewire 12 to the target location in the lumen 4, it is the only stent engaged with the guidewire 12, i.e., there are no other stents engaged with the guidewire between the stent 52 and the proximal end of the guidewire 12.

According to embodiments, it can be desirable to deploy more than one stent in the lumen, for example if more than stent is required to fully support a blocked passage in a duct. Thus, it may be that two, three or even more biliary stents are deployed, generally alongside one another, in the same lumen and in roughly the same portion of the lumen. The stents can all be the same size, or they can be of varying sizes. In some cases, a surgeon can accurately predict in advance how many stents (and of which sizes) are to be deployed, and, in some cases, it can happen that after one stent is deployed, or after two or more stents are deployed, a need for deploying yet another stent can be seen.

Deployment of multiple stents according to the present invention can be handled using various methods.

In a first multiple-stent deployment method, the method disclosed hereinabove for deploying a single stent using the stent-conveyance tube 220 (as described in Steps S01 . . . S04) can be repeated. Once the stent-conveyance tube 220 has been completely withdrawn, leaving the guidewire 220 in place in accordance with the disclosed embodiments, an additional stent assembly 101 comprising a stent 52 mounted on a stent-conveyance tube 220 is advanced along the guidewire 12 to a target location in the lumen 4, i.e., alongside the already-deployed first stent 52. The method can be repeated as many times as are necessary.

In a second multiple-stent deployment method, two stents 52, 54 are deployed using a single stent assembly that additionally comprises a second stent 54. (The stent 52 described with respect to FIGS. 1-4D is the 'first' stent according to this method and configuration). As seen in the flowchart of FIG. 5, the second multiple-stent deployment method comprises the following steps:

Steps S01 and S02, as described hereinabove, in either order;

Step S05 threading the guidewire through the tube segment on which the second stent is mounted or is to be mounted. The guidewire 12 preferably enters/re-enters the interior of the tube 220 through aperture 400 as seen in FIGS. 4A-4D; and Step S06 arranging the second stent 54 so as to surround a segment of the tube proximal of the first stent 52. In embodiments, there is an intermediating gap between the first and second mounted stents, for example to permit the guidewire 12 to pass through aperture 400 into the interior of the tube 220, including the interior of the segment on which the second stent is mounted. The guidewire 12 need not exit the tube 220 again between aperture 400 and the proximal end of the tube 220.

Figure 5:
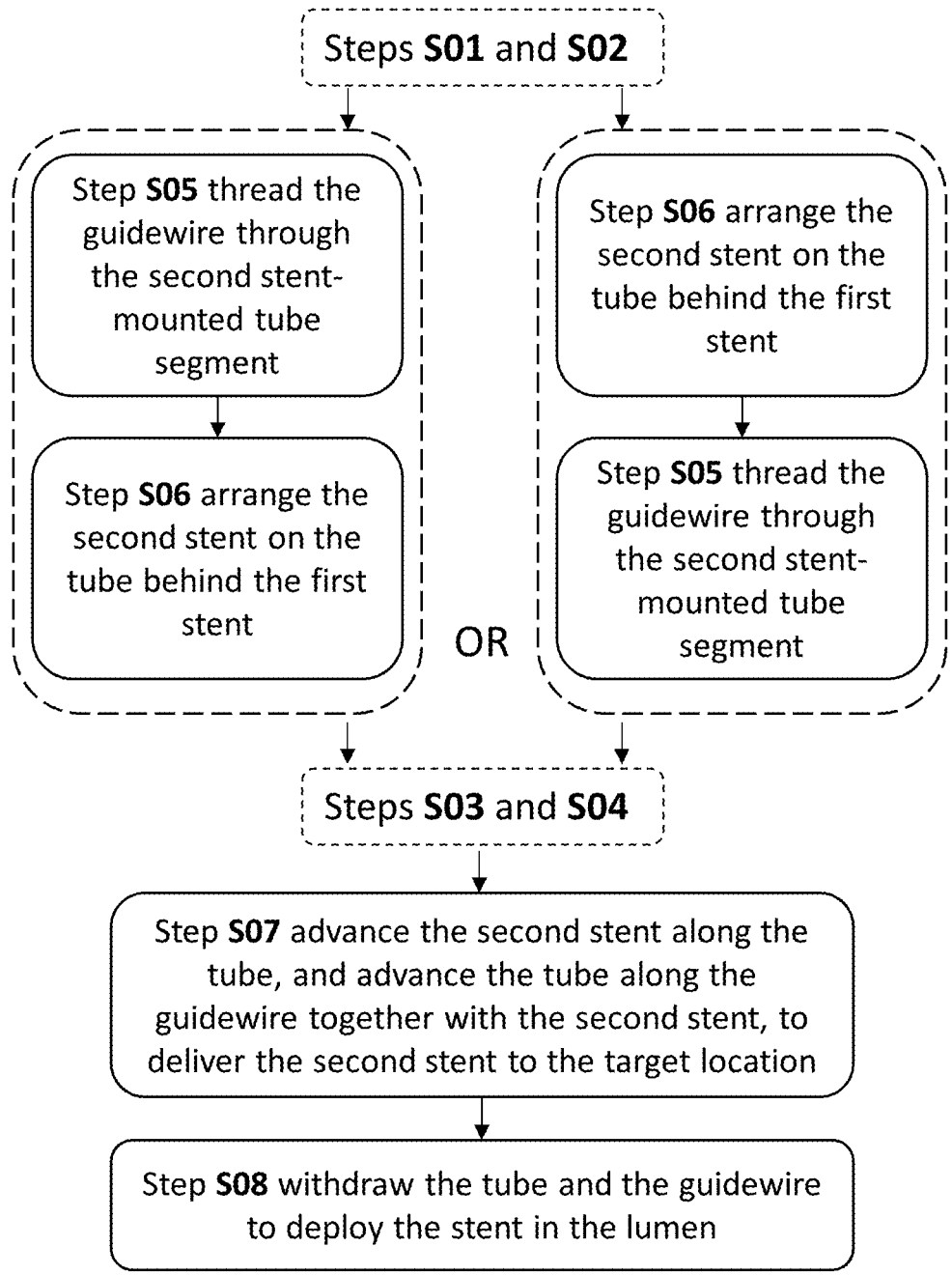
FIG. 5 shows a flowchart of a method for deploying multiple stents in a lumen of a human subject, in accordance with embodiments of the present invention.

As shown in the flowchart of FIG. 5, Steps S05 and S06 can be carried out in either order, i.e., first Step S05 and then Step S06, or first Step S06 and then Step S05.

After carrying out Steps S01, S02, S05 and S06 the stent assembly 101 can be seen to be in a 'dual-stent stent-advancement configuration' in which the guidewire 12 first passes through the distal and proximal apertures 320, 262 so as to interiorly traverse the guidewire-retaining segment 222, the first stent 52 is arranged to surround a stent-conveyance tube segment that is proximally displaced from the guidewire-retaining segment 222, the guidewire 12 is further passed through aperture 400 between the two stents 52, 54 so as to interiorly traverse the portion of the tube 220 that is proximal thereto, and the second stent is arranged to surround a second stent-conveyance tube segment that is proximally displaced from the first stent 52 and from aperture 400. The dual-stent stent-advancement configuration is suitable for advancement of the first and second stents 52, 54 together with the stent-conveyance tube 220 along the guidewire 12 into a body lumen of a human subject.

The method additionally comprises:

Steps S03 and S04, as described hereinabove;

Step S07 advancing the second stent along the tube, and advancing the tube along the guidewire together with the second stent, to deliver the second stent to the target location; and Step S08 withdrawing the tube and the guidewire to deploy the stent in the lumen.

Steps of the instant method for deploying multiple biliary stents in a lumen of a human body will be explained in greater detail in connection with FIGS. 6A-E.

Figure 6A:
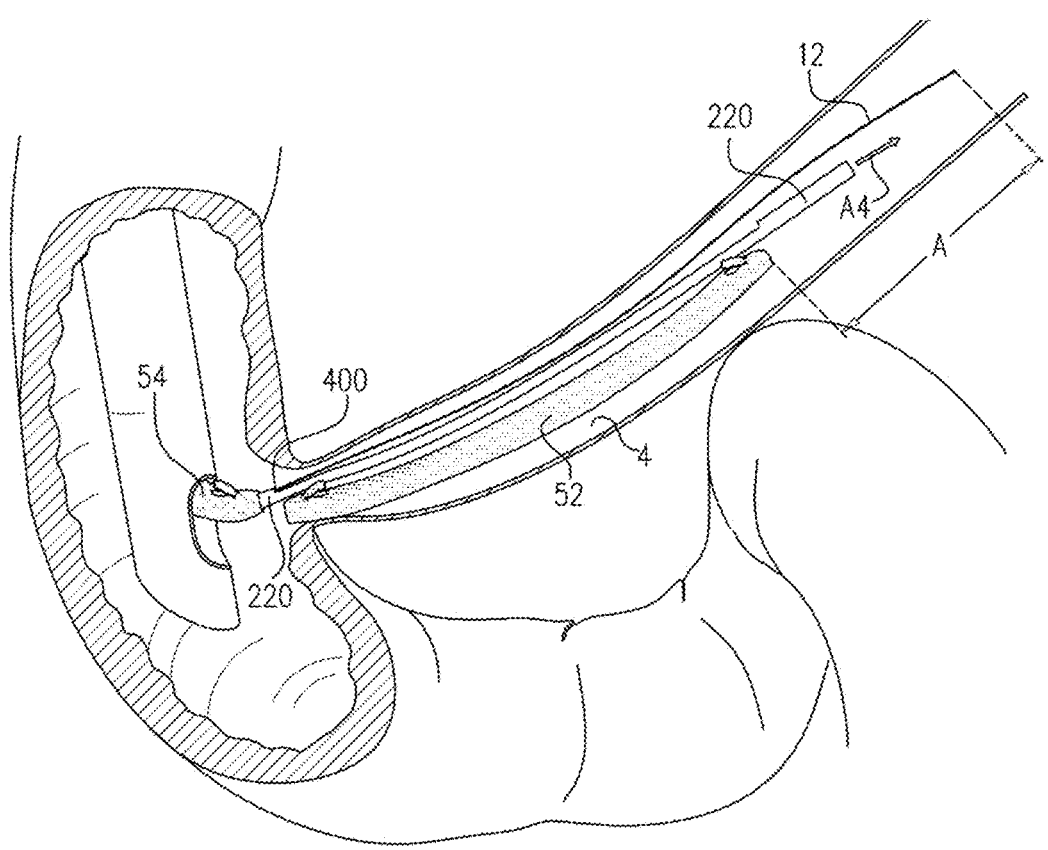
FIGS. 6A-6E are schematic illustrations depicting a general overview of a method for deploying multiple stents in a lumen of a subject, in accordance with embodiments of the present invention.

FIG. 6A shows the positions of first and second stents 52, 54 after Step S04 and before Step S07. Stent 52 is deployed in the lumen 4, and guidewire 12 is disengaged from the stent-conveyance tube 220. Unlike FIG. 4D, which illustrated an embodiment in which the (first) stent 52 was the only stent engaged with the guidewire 12, in FIG. 6A the second stent 54 can be seen as mounted on the tube segment proximal to aperture 400. Optionally, tube 220 can be advanced distally in the direction indicated by arrow A4.

It is additionally noted with respect to FIG. 4A, that in accordance with some embodiments, there is a fixed distance of at least 1 mm and/or not more than 80 mm between the first stent 52 and the second stent 54 (not shown in FIG. 7B) due to locking of the second stent 54 such that it is prevented from distal motion, prior to deployment of first stent 52. An example of such a locking mechanism is described hereinbelow with reference to FIGS. 8A-8D. In some embodiments, the fixed distance is at least 5 mm, and for some applications, the fixed distance is no more than less than 25 mm.

Figure 6B:
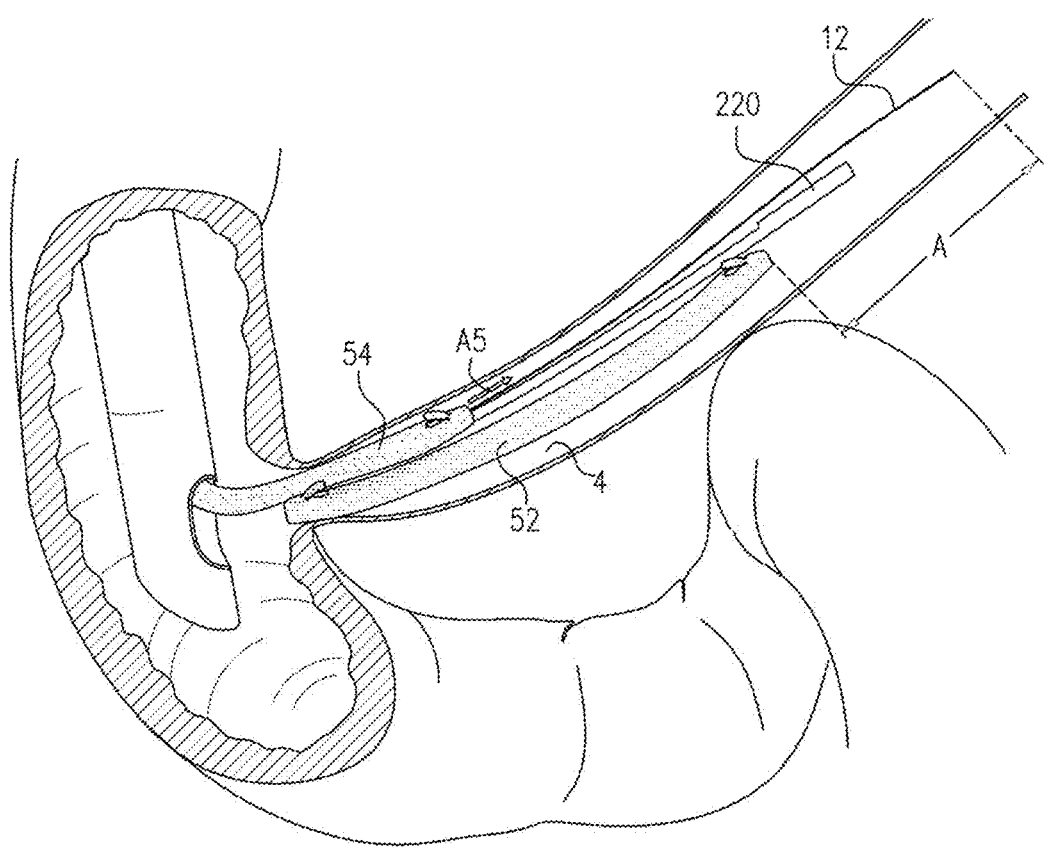

Referring now to FIG. 6B, the second stent 54 is shown (as indicted by arrow A5) as having advanced over stent-conveyance tube 220 and over guidewire 12 as well, while Step S07 is carried out. At this point in time, the distal end of second stent 54 has advanced distally from aperture 400, which can no longer be seen in FIG. 6B. It is noted that during the Step S07 deployment of the second stent 54, the guidewire 12 is maintained within lumen 4 and is not advanced proximally or distally in the lumen 4, at least not for purposes of carrying out the instant method.

Figure 6C:
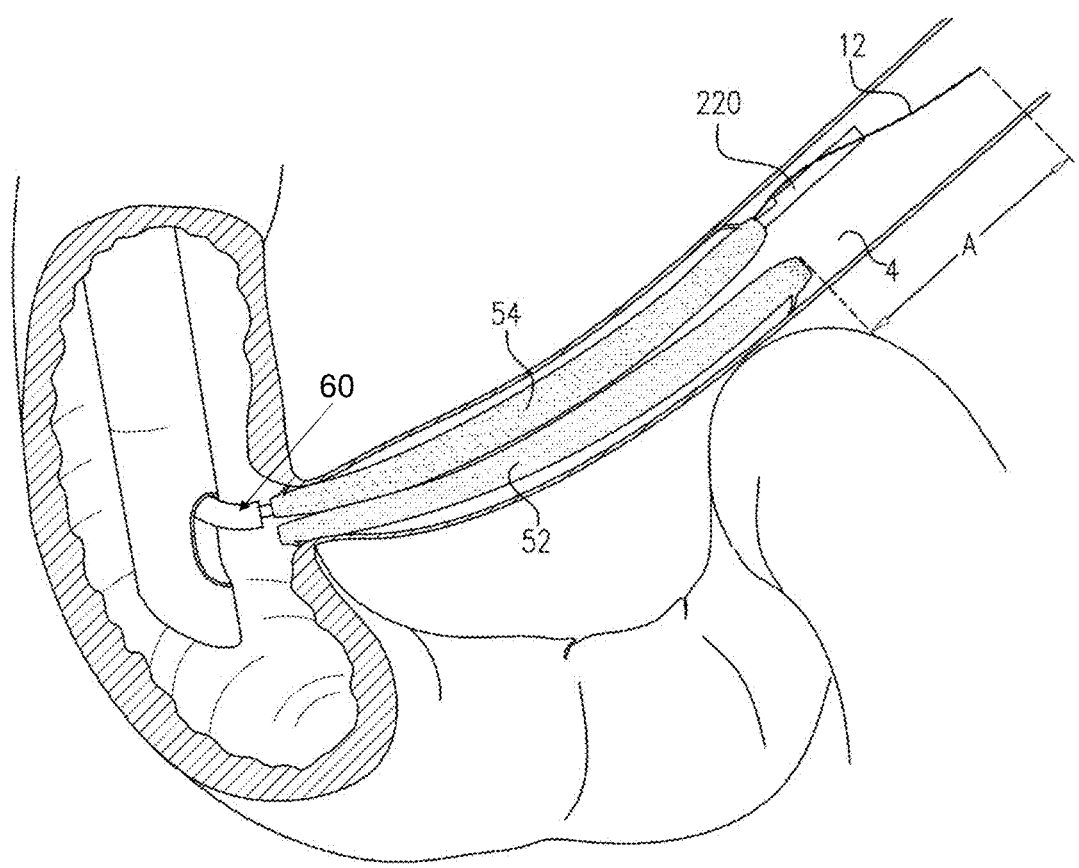

In FIG. 6C, the position of the second stent 54 at the end of Step S07 is shown. The second stent has been advanced into the target location alongside the first stent 52 in the lumen 4. In some embodiments, as illustrated in FIG. 6C, a pusher tube 60 can be used to facilitate the distal advancement of the second stent 54 along the stent-conveyance tube, and/or to facilitate 'pushing' the second stent 54 off the distal end of the tube 220 when the tube 220 is proximally withdrawn in Step S08.

Figure 6D:
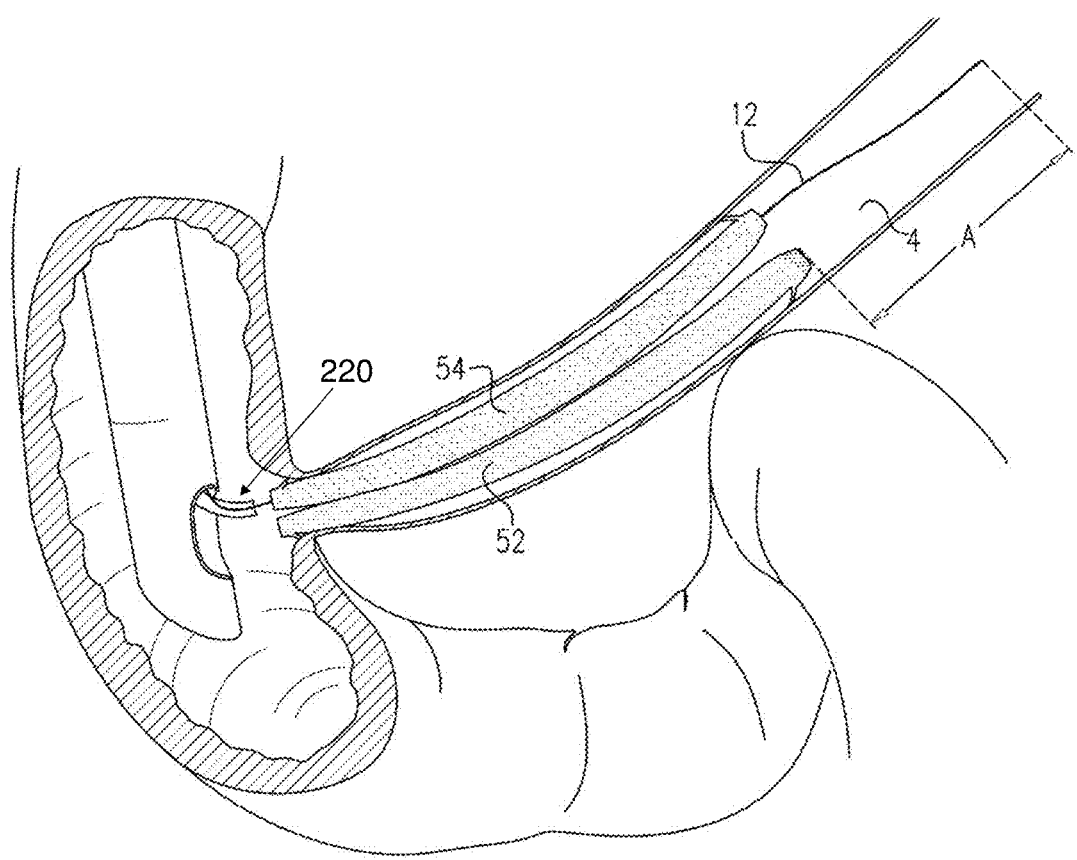
Figure 6E:
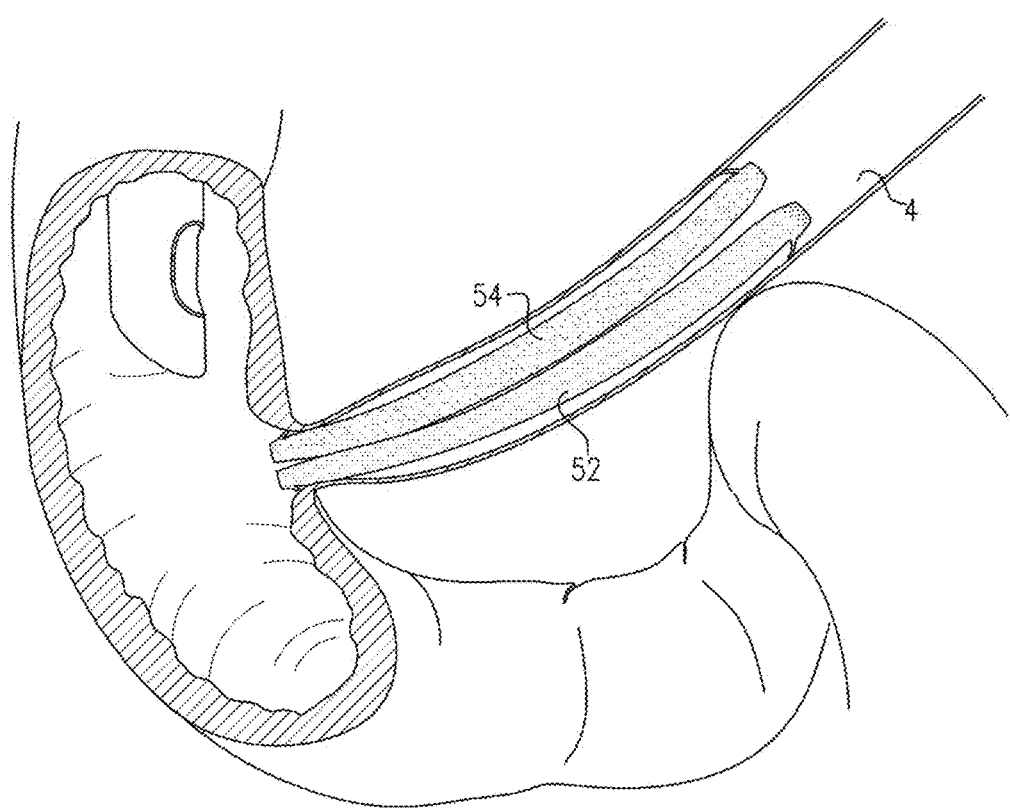

The carrying out of Step S08 is illustrated in FIGS. 6D-6E. In FIG. 6D, the stent-conveyance tube 220 can be seen to have been withdrawn from within the second stent 54, now anchored in the lumen. Finally, in FIG. 6E, it can be seen that the guidewire 12 has been withdrawn as well.

From the foregoing discussions, it will be obvious to the skilled artisan that various methods may be used for deploying three stents, including, without limitation: employing the first method (Steps S01 . . . S04) of deploying a single stent, three times (once for each stent), aided by the same guidewire each time, the guide wire remaining in place after at least the first and second stents have been deployed; and employing said first method of deploying a single stent, the guidewire remaining in place thereafter, and subsequently employing the method of deploying two stents (Steps S01 . . . S08).

Discussion of Stent-Locking Mechanisms

Reference is now made to FIGS. 7A-7B and 8A-8D, which are schematic illustrations of locking mechanisms configured to prevent motion of first stent 52 and, optionally, second stent 54, with respect to the guide tube. The locking mechanisms are typically employed in order to allow stents to be advanced together with the guide tube in a controlled manner within the lumen of the subject. Once the physician removes each locking mechanism, the respective stent can be deployed off the distal end of the guide tube in the lumen. The specific design example described hereinbelow is meant to be illustrative and not limiting. Moreover, the description generally relates to embodiments in which two stents 52, 54 are employed together for deployment according to the method described hereinabove with respect to Steps S01 . . . S08, but is equally applicable, with necessary modifications, to the single-stent configurations and methods described hereinabove.

Reference is first made to a first lock 600 for preventing proximal and distal motion of first stent 52 with respect to tube 220, as illustrated in FIGS. 7A, 7B, 8A and 8D. First lock 600 is configured to prevent proximal motion of the first stent 52 past a location that is at least 1-80 mm (e.g., 2-80 mm, e.g., 5-80 mm, e.g., 5-mm) distal to the distal end of second stent 54 if present. Additionally, first lock 600 is configured to prevent distal motion of stent 52, such that stent 52 does not slip off the distal end of the stent-conveyance tube 220 while it is being advanced in the lumen 4 of the subject until a desired implantation location is reached, and the physician removes first lock 600.

Typically, first lock 600 comprises a first locking wire 610 and a locking loop 620.

Figure 8A:
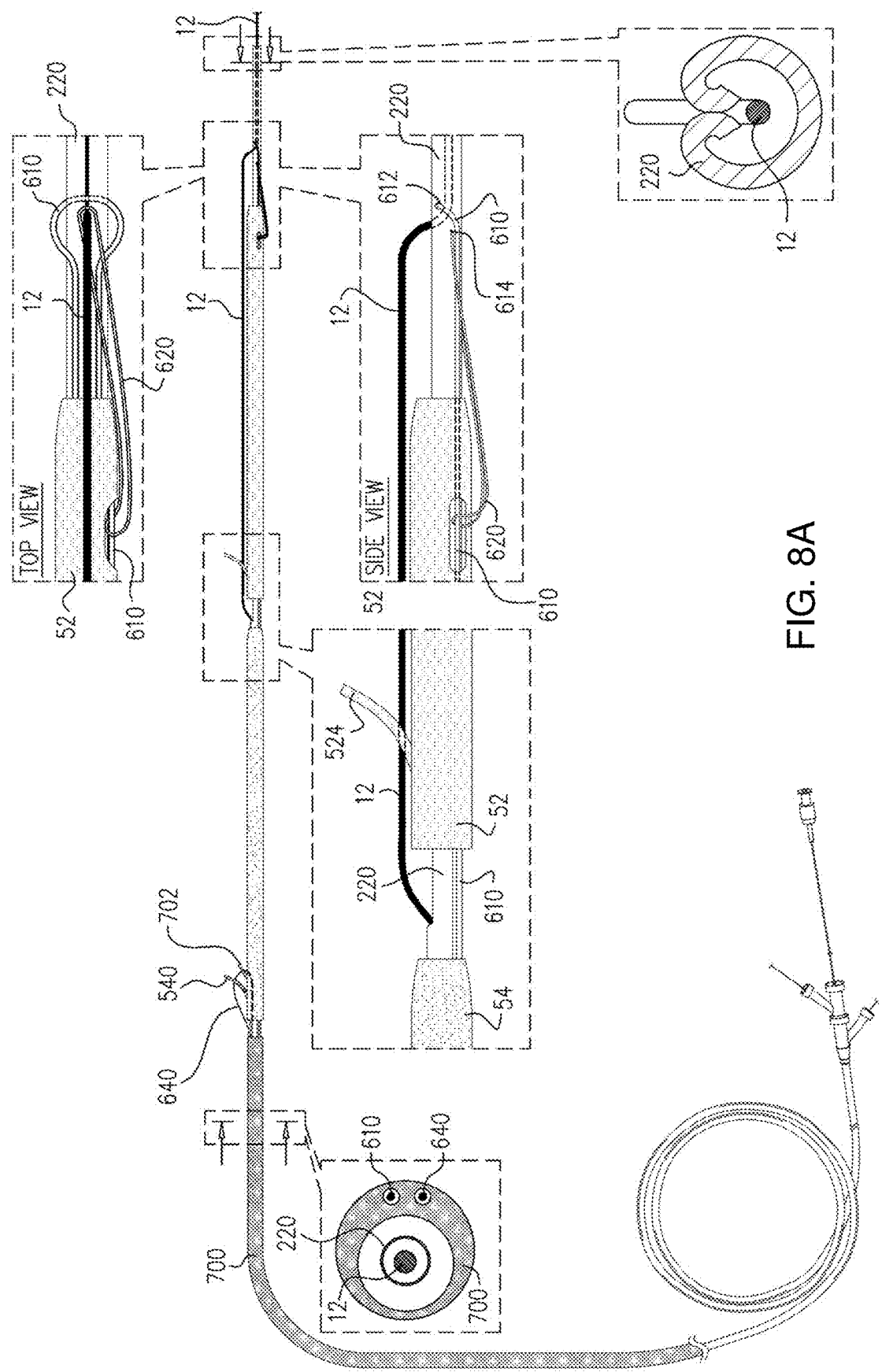
FIGS. 8A-8D are schematic illustrations of locking mechanisms comprising first and second locks configured to prevent motion of the first stent and the second stent, respectively, with respect to the guide tube.
Figure 8B:
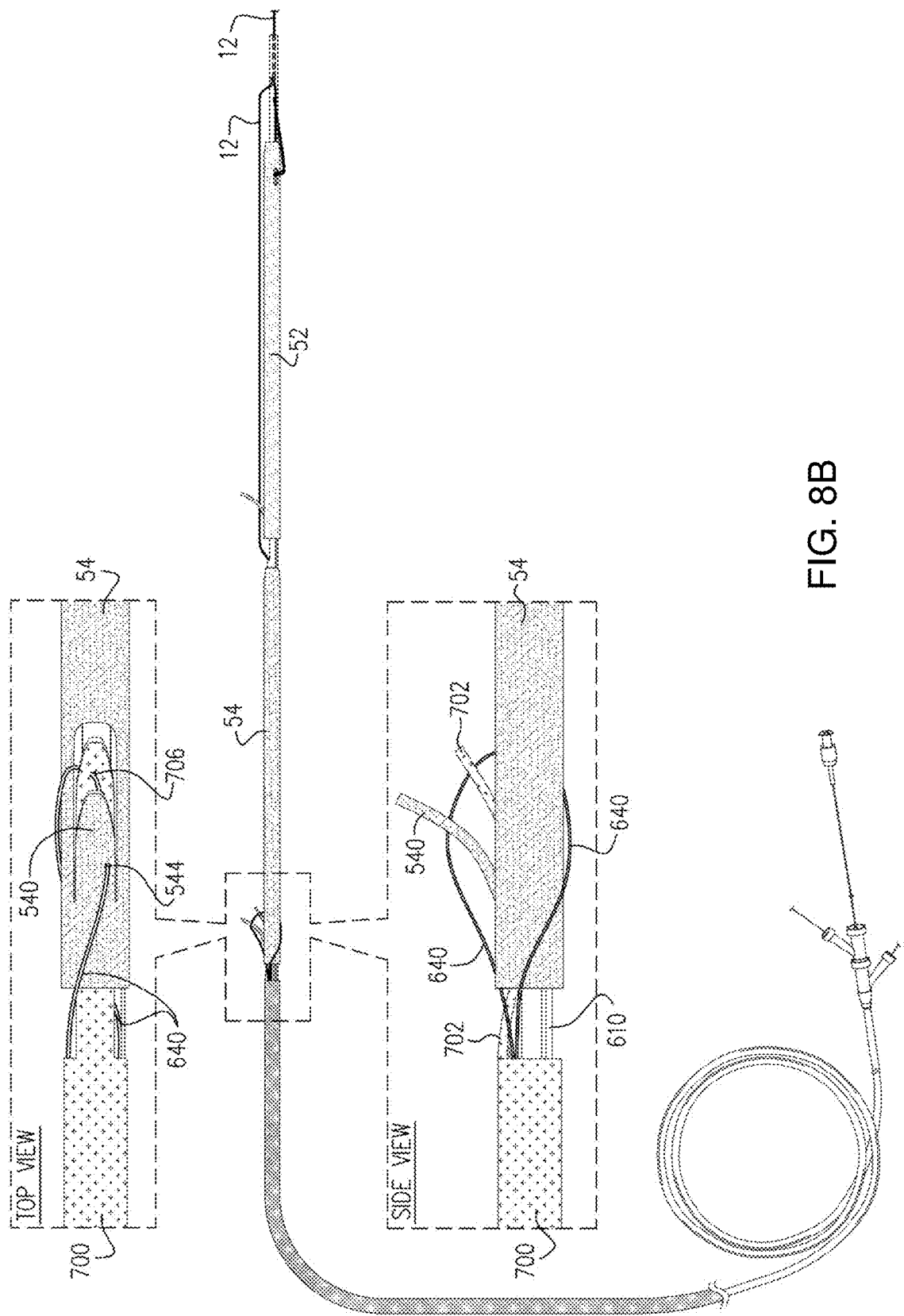
Figure 8C:
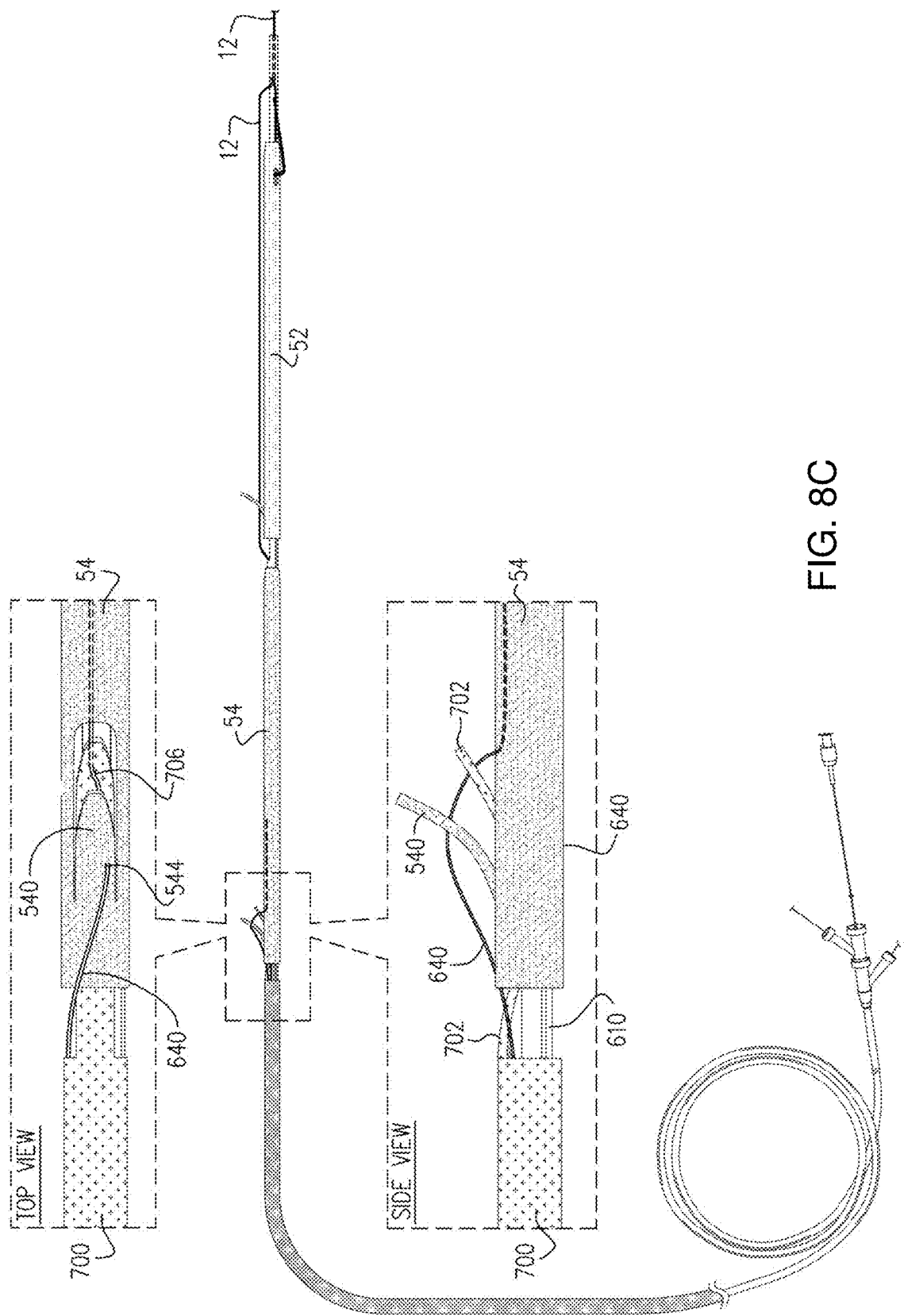
Figure 8D:
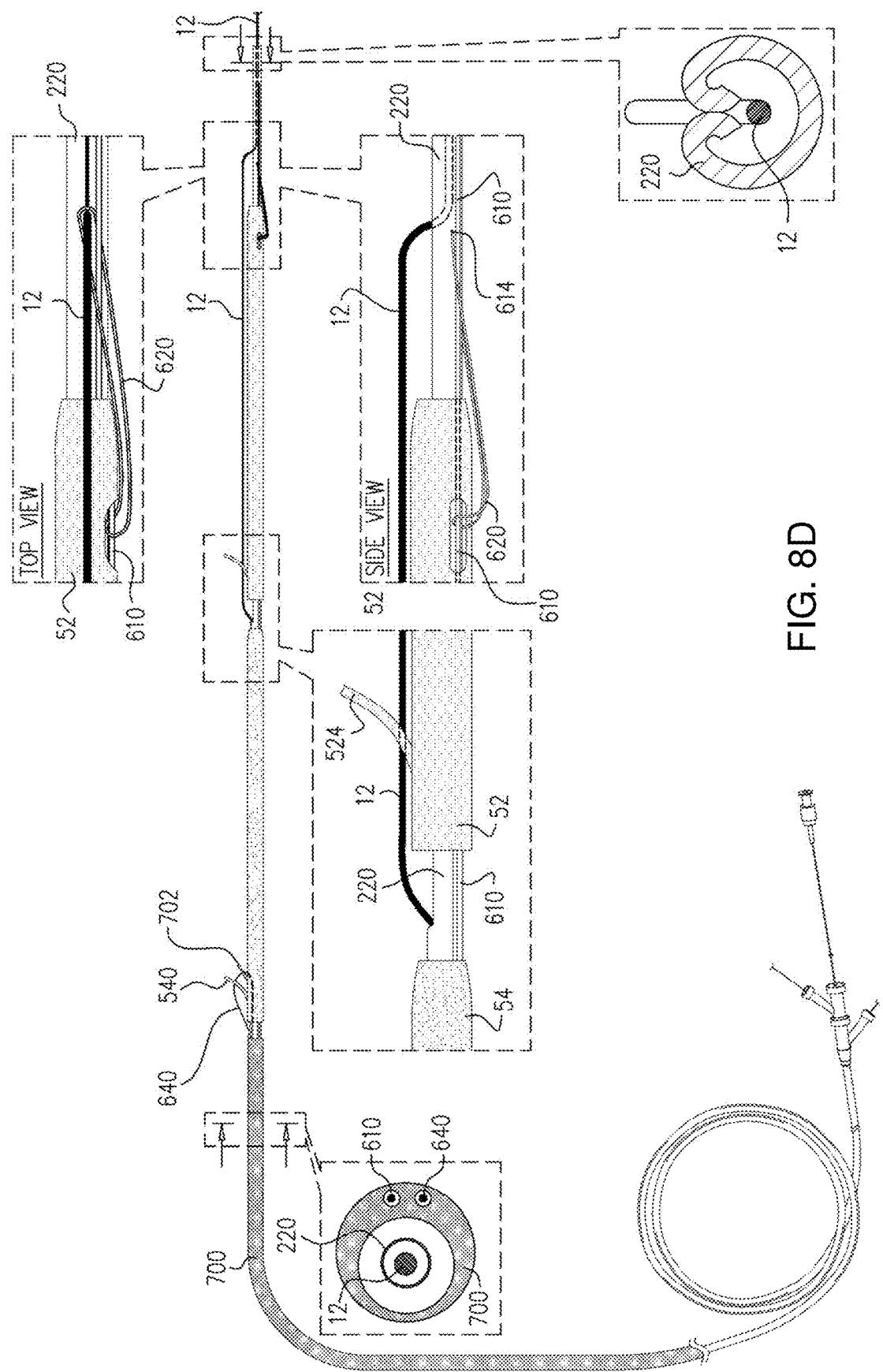

Locking loop 620 is typically secured to tube 220 by the loop being looped through two lateral holes 614 provided in the stent-conveyance tube 220, shown in FIGS. 8A and 8D).

First locking wire 610 typically comprises a thin metal or polymer wire having a diameter of 0.1-0.35 mm, e.g., 0.2 mm. First locking wire 610 typically runs from the proximal portion of the stent assembly 101 between tube 220 and an inner surface of first and second stents 52 and 54, and is threaded through locking loop 620 (typically being accessed by locking loop 620 via a hole in the wall of first stent 52).

Figure 7A:
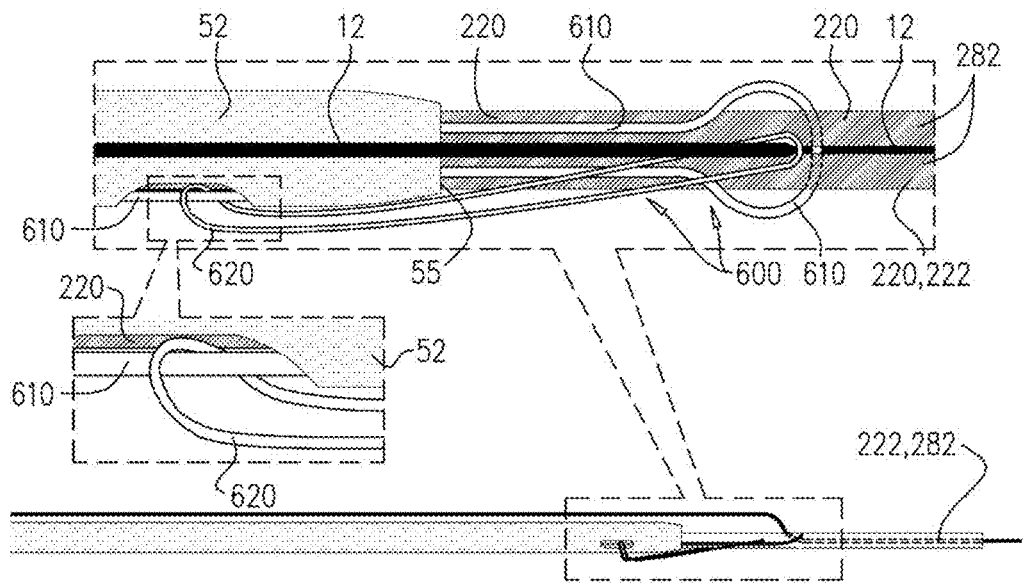
FIGS. 7A-7B are schematic illustrations of a locking mechanism comprising a lock configured to prevent motion of the first stent with respect to the guide tube.

First locking wire 610 exits first stent 52 through distal end 55 of stent 52 and is disposed adjacent to the side of guide tube 220 distal to distal end 55. For some applications, such as is shown in FIGS. 7A and 8A, locking wire 610 passes through a lateral hole 612 in the side of the tube 220, travels across the tube 220, and leaves the tube 220 via an additional lateral hole 612 in the opposite side. Locking wire 610 then runs proximally along the inner surface of first stent 52, outside of the tube 220. This locks first stent 52 in place and prevents distal or proximal motion of the stent 52. Additionally, in embodiments using the slit 280/slit-lips 282 design, when first locking wire 610 passes through lateral holes 612, slit lips 282 are brought in contact with each other, to maintain slit 280 in a closed state.

Figure 7B:
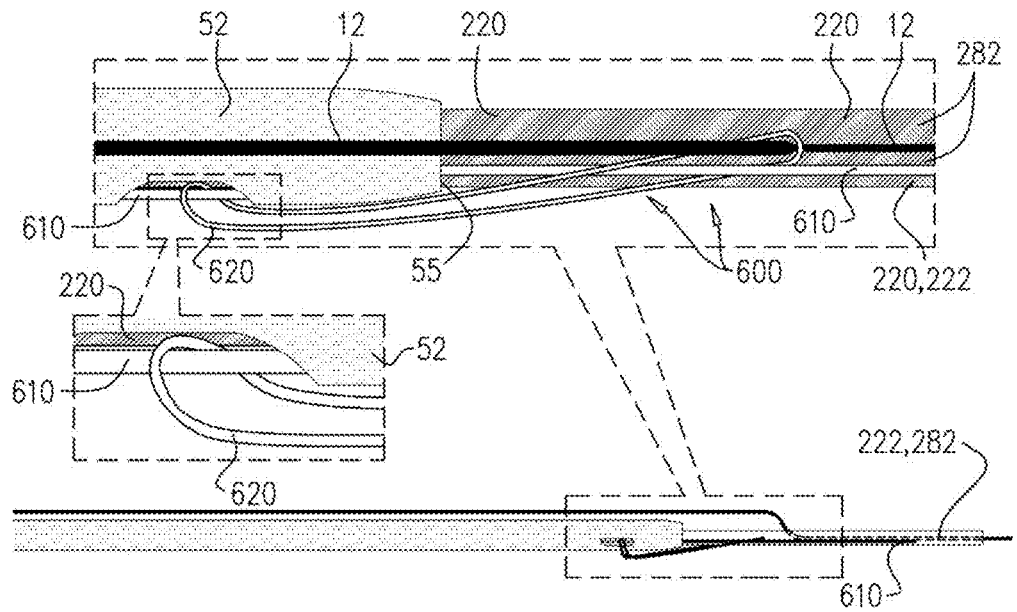

Alternatively, such as is shown in FIGS. 7B and 8D, after locking wire 610 is threaded through locking loop 620, locking wire 610 continues to run distally outside of the tube 220.

Once stent 52 is in the desired location in the lumen of the subject, the physician pulls first locking wire 610 proximally, thereby releasing the locking of first stent 52 by disengaging locking wire 610 from locking loop 620. This disengaging allows proximal motion of the tube 220, whereby first stent 52 is deployed distally off guide tube 220, e.g., in Step S04 of FIG. 3 or FIG. 5.

Reference is now made to a second lock comprising locking wire 640 for preventing distal motion of second stent 54 with respect to stent-conveyance tube 220, as illustrated in FIGS. 8B and 8C.

As shown in FIG. 8B, second stent 54 is shaped to define a hole 544 in a portion of second stent 54 (e.g., in anchor flap 540). Additionally, a pusher tube 700 disposed proximally to second stent 54 and configured to push second stent 54 off of guide tube 220, is shaped to define a hole 706 in a portion of the pushing tube (e.g., in a distal extension portion 702 of the pushing tube).

Second locking wire 640 passes through the hole 544 in the portion of second stent 54 and through hole 706 in the portion 702 of pusher tube 700 to prevent distal motion of stent 54. Subsequently to deployment of first stent 52, second locking wire 640 is removed from holes 544 and 706, releasing second stent 54 from being locked. Subsequently, second stent 54 is deployed off the distal end of guide tube 220.

For some applications, such as is shown in FIG. 8B, after passing through holes 544 and 706, second locking wire 640 loops back towards pusher tube 700, and then runs proximally along the inner surface of pusher tube 700, outside of guide tube 220.

Alternatively, as is shown in FIG. 8C, after passing through holes 544 and 706, second locking wire 640 continues to run distally along the inner surface of second stent 54, outside of the tube 220.

It is noted that first lock 600 is not arranged to utilize guidewire 12 to prevent distal, or proximal motion of first stent 52. It is additionally noted that locking wire 640 is not arranged to utilize guidewire 12 to prevent distal motion of second stent 54.

In some embodiments, locking wires 610 and 640 can be disposed in respective lumens in a wall of pusher tube 700.

Figure 9A:
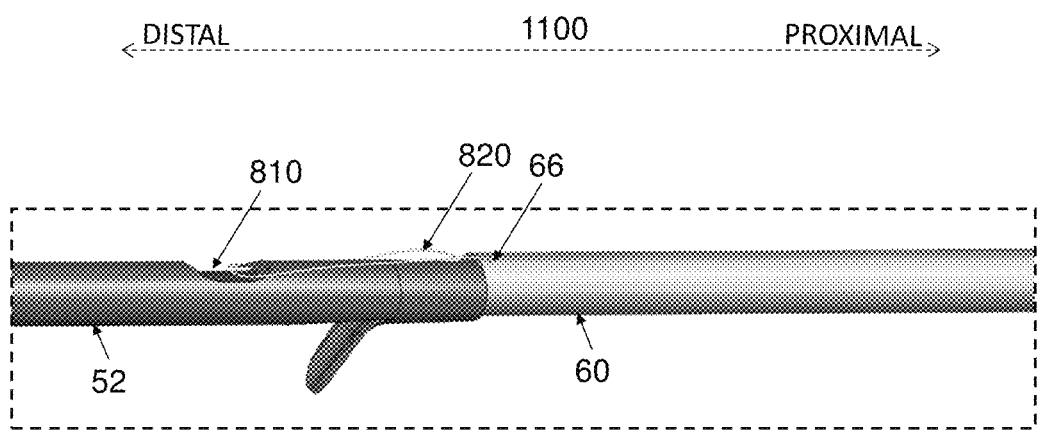
FIGS. 9A-9B are schematic illustrations of a locking mechanism engaging a stent with a pushing tube.
Figure 9B:
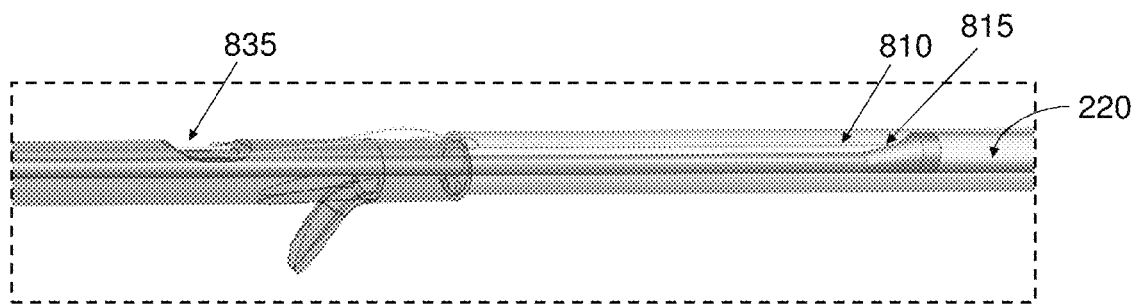

We now refer to FIGS. 9A and 9B. FIG. 9B is approximately the same illustration as FIG. 9A but with some of the outer surfaces made transparent for better understanding the interior elements in the illustration. FIGS. 9A and 9B illustrate a proximally withdrawable locking mechanism. This mechanism can be used to maintain a position of a stent 52 relative to the stent-conveyance tube 220 when the stent-deployment assembly is advanced along the guidewire 12.

A stent 52 is arranged to surround a portion of a stent-conveyance tube 220. A pushing tube 60 is arranged to surround a portion of a stent-conveyance tube 220 proximal to the stent 52. The distal and proximal directions for FIGS. 9A-9B are indicated by arrow 1100. A first locking member 810 is engaged at a proximal end with the stent-conveyance tube 220 at engagement point 815. An example of a suitable first locking member 810 is a wire comprising a metal or a metal allow. The engagement of the first locking member 810 with the stent-conveyance tube 220 can include any kind of permanent or temporary attachment. A second locking member 820 enters the pushing tube 60 through a hole 66, traverses a portion of the pushing tube 60 transversely, and exits through a second hole 66 (not visible in FIGS. 9A-9B). A loop portion of the second locking member 820 which is external to the pushing tube 60, is threaded under the first locking member 810 in stent-opening 835. The loop portion of the second locking member 820 is illustrated schematically as a loose loop but in actual implementation is preferably a tight loop so as to maintain the position of stent 52 when the stent-conveyance tube 220 is advanced together with the stent 52 and the pushing tube 60 along a guidewire 12 (not shown in FIGS. 9A-9B. The loop portion is preferably installed tightly enough that the presence of the second locking member 820 doesn't allow the stent-conveyance tube 220 and the pushing tube to separate from each other at all (or by more than 1 mm, or by more than 2 mm) as the loop portion is 'trapped' between the first locking member 810 and a proximal edge of the hole 835. The design of the proximally withdrawable locking mechanism is such that a proximal withdrawal of the stent-conveyance tube 220 is effective to pull the first locking member 810 (which is engaged with the stent-conveyance tube 220) proximally, so as to disengage (free) the loop portion of the second locking member 820 so that the stent 52 and pushing tube 60 are freely separable, e.g., the stent 52 can be deployed in the lumen of the subject.

The scope of the present invention includes use of stents and stent assemblies in any suitable lumen to deploy multiple stents, tubes, or other apparatus in the lumen. For example, techniques and apparatus described herein may be used in a urethra, and/or in a ureter, and/or in a pancreatic duct, and/or in an esophagus, and/or in a trachea of the subject. Additionally, or alternatively, techniques and apparatus described herein may be used to deploy two or more prostatic stents.

Additional Discussion

In accordance with some applications of the present invention, apparatus and methods are provided for deployment of more than one stent (e.g., two stents) within a lumen of a subject. For example, two or more stents are deployed within a common bile duct of a subject in order to treat biliary strictures and obstructions. Typically, the two or more stents, e.g., two, three or four stents, are deployed alongside each other within the common bile duct to facilitate relieving of the biliary stricture. Typically, a guide tube is used to deploy the stents (e.g., a first and a second stent) in the lumen of the subject. In this context, in the specification and in the claims, "proximal" means closer to the orifice through which the guide tube or stent is originally placed into the body, and "distal" means further from this orifice.

For some applications, the guide tube is shaped to define a guidewire-engaging portion, e.g., a slit, extending proximally along the wall of the guide tube, from the distal end of the guide tube. A proximal end of the slit is typically located distally to the proximal end of the guide tube. Additionally, the guide tube is shaped to define a hole through a wall of the guide tube, the hole being located proximally to the proximal end of the guidewire-engaging portion and distally to the proximal end of the guide tube. Typically, a proximal end of the slit is located distally to the hole.

During delivery into the lumen of the subject, the first stent surrounds the guide tube and is advanced together with the guide tube into the lumen of the subject. Typically, the first stent is disposed along the guide tube such that, prior to insertion into the subject's body, a proximal end of the first stent is disposed distally to the hole in the wall of the guide tube while a distal end of the first stent is disposed proximally to the guidewire-engaging portion. When positioned at a desired site within the lumen of the subject, the first stent is slidably deployed from, i.e., advanced off of, the distal end of the guide tube and deployed within the lumen.

Also prior to insertion into the subject's body, the second stent is disposed proximal to the first stent, surrounding a proximal portion of the guide tube. (The proximal portion of the guide tube is called the "proximal portion" because it is proximal to the more distal portion of the guide tube, around which the first stent is disposed. The proximal portion of the guide tube, as well as the second stent surrounding the proximal portion of the guide tube, is introduced into the subject's body, as described herein.) The second stent is shaped and sized to be advanced over the guide tube and off of the distal end of the guide tube into the lumen of the subject. The second stent is placed alongside the first stent subsequently to deployment of the first stent off of the distal end of the guide tube.

In accordance with some applications of the present invention, the first and second stents are delivered to the lumen of the subject without removing the guide tube or a guidewire used during the procedure from the body of the subject following deployment of the first stent and prior to deploying the second stent. As provided by some applications of the present invention, the first and second stents are both pre-mounted onto the guide tube and advanced into the subject's body in one advancement procedure, to be deployed subsequently within the lumen of the subject, as described herein.

There is therefore provided in accordance with some applications of the present invention, apparatus, including: a guide tube shaped to define (a) a guidewire-engaging portion at a distal portion of the guide tube, a proximal end of the guidewire-engaging portion being located distally to a proximal end of the guide tube, (b) a hole in a wall of the guide tube, the hole being located proximally to the proximal end of the guidewire-engaging portion and distally to a proximal end of the guide tube; a first stent surrounding the guide tube so as to be advanceable together with the guide tube into a lumen of a subject, the first stent being slidable along the guide tube such that a proximal end of the first stent is disposable distally to the hole while a distal end of the first stent is disposed proximally to the guidewire-engaging portion, the first stent being slidably deployable off of the distal end of the guide tube; and a second stent, proximal to the first stent, surrounding a proximal portion of the guide tube, and shaped and sized to be advanceable along the guide tube and deployable off of the distal end of the guide tube into the lumen and placed alongside the first stent subsequently to deployment of the first stent off of the distal end of the guide tube. For some applications, a distal end of the second stent is disposed proximally to the hole.

For some applications the apparatus further includes a guidewire configured to (i) enter a lumen of the guide tube from a distal-end opening of the guide tube, (ii) pass out of the lumen of the guide tube at the guidewire-engaging portion of the guide tube, and (iii) pass into the lumen of the guide tube through the hole, and the first stent is (i) constrained from distal motion past the guidewire-engaging portion when the guidewire is disposed within the guidewire-engaging portion, and (ii) constrained from proximal motion past the hole when the guidewire is disposed within the hole.

For some applications, the first stent is slidably deployable off the distal end of the guide tube when the guidewire is not disposed within the guidewire-engaging portion. For some applications, there is no hole in the wall of the guide tube that is within 10 mm from the distal end of the guide tube. For some applications, there is no hole having a diameter of less than 1 cm in the wall of the guide tube that is within 10 mm from the distal end of the guide tube For some applications the apparatus further includes a guidewire that (i) enters a lumen of the guide tube from a distal-end opening of the guide tube, (ii) passes out of the lumen of the guide tube at the guidewire-engaging portion of the guide tube, and (iii) passes into the lumen of the guide tube through the hole, and the first stent (a) has an outer surface disposed against the guidewire and (b) is configured to be advanced into the lumen of the subject while the outer surface is disposed against the guidewire, and the second stent, surrounds the guidewire, and is configured to be advanced into the lumen of the subject over the guidewire.

For some applications, a distance between the distal end of the guide tube and the hole is 4-18 cm. For some applications, the guidewire-engaging portion is shaped to define a slit extending proximally along the wall of the guide tube, from the distal end of the guide tube, the slit having a length of 1 mm-7 cm. For some applications, the slit has a length of 2.5-3 cm. For some applications, the guidewire-engaging portion is shaped to define a weak spot configured to tear in response to force applied to the weak spot by a guidewire.

There is further provided in accordance with some applications of the present invention, apparatus including: a guide tube shaped to define a proximal end and a distal end of the guide tube; a first stent surrounding the guide tube so as to be advanceable together with the guide tube into a lumen of a subject, and being slidably deployable off of the distal end of the guide tube; a second stent, proximal to the first stent, surrounding a proximal portion of the guide tube, and shaped and sized to be advanceable along the guide tube into the lumen; a first lock, which prevents proximal motion of the first stent past a location that is at least 1 mm from a distal end of the second stent; and a second lock, which prevents distal motion of the second stent past a location that is at least 1 mm proximal of a proximal end of the first stent. For some applications, the guide tube is shaped to define two holes in a lateral wall of the guide tube, and the first lock includes a locking wire that passes through the two holes.

For some applications: the second stent is shaped to define a hole in a portion of the second stent, the apparatus further includes a pushing tube, disposed proximally to the second stent and configured to push the second stent off of the guide tube, the pushing tube is shaped to define a hole in a portion of the pushing tube, and the second lock includes a locking wire that passes through the hole in the portion of the second stent and through the hole in the portion of the pushing tube.

For some applications, the first lock includes a first locking wire, and the second lock includes a second locking wire. For some applications, a distance between the proximal end of the first stent and the distal end of the second stent is a fixed distance. For some applications, a distance between the proximal end of the first stent and the distal end of the second stent is 2-80 mm. For some applications, the distance between the proximal end of the first stent and the distal end of the second stent is at least 5 mm. For some applications, the distance between the proximal end of the first stent and the distal end of the second stent is less than mm.

For some applications, the first lock is configured to prevent distal motion of the first stent during advancement of the first stent on the guide tube into the lumen of the subject.

For some applications the apparatus further includes a guidewire, the guide tube is further shaped to define (a) a guidewire-engaging portion at a distal portion of the guide tube, a proximal end of the guidewire-engaging portion being located distally to a proximal end of the guide tube, and (b) a hole in a wall of the guide tube, the hole being located proximally to the proximal end of the guidewire-engaging portion and distally to a proximal end of the guide tube, the first stent is (i) constrained from distal motion past the guidewire-engaging portion when the guidewire is disposed within the guidewire-engaging portion, and (ii) constrained from proximal motion past the hole when the guidewire is disposed within the hole, and the first lock is not arranged to utilize the guidewire to prevent distal motion of the first stent.

There is further provided in accordance with some applications of the present invention, apparatus including: a guide tube shaped to define a proximal end and a distal end of the guide tube; a first stent surrounding the guide tube so as to be advanceable together with the guide tube into a lumen of a subject, and being slidably deployable off of the distal end of the guide tube; a second stent, proximal to the first stent, surrounding a proximal portion of the guide tube, and shaped and sized to be advanceable along the guide tube into the lumen; and a lock, which prevents distal motion of the second stent beyond a proximal end of the first stent when the first stent is being slidably deployed off of the distal end of the guide tube, and unlockable subsequently to the deployment of the first stent off of the distal end of the guide tube to allow deployment of the second stent off of the guide tube.

For some applications: the second stent is shaped to define a hole in a portion of the second stent, the apparatus further includes a pushing tube, disposed proximally to the second stent and configured to push the second stent off of the guide tube, the pushing tube is shaped to define a hole in a portion of the pushing tube, and the second lock includes a locking wire that passes through the hole in the portion of the second stent and through the hole in the portion of the pushing tube.

There is further provided in accordance with some applications of the present invention, a method including: using apparatus including: a guide tube shaped to define a proximal end and a distal end of the guide tube; a first stent surrounding a distal portion of the guide tube, and a second stent, proximal to the first stent, surrounding a proximal portion of the guide tube; advancing the apparatus to a desired location in a lumen of a subject while: (a) the first stent is constrained from proximal motion past a location that is at least 1 mm from a distal end of the second stent, and (b) the second stent is constrained from distal motion beyond a location that is at least 1 mm proximal of a proximal end of the first stent.

For some applications: subsequently to the advancing of the apparatus, and while the second stent is constrained from distal motion, withdrawing the guide tube with respect to the first stent, until the first stent is deployed off of the distal end of the guide tube into the lumen; subsequently to deploying the first stent off of the distal end of the guide tube, releasing the second stent such that it is not constrained from distal motion; subsequently, advancing the second stent along the guide tube in the lumen of the subject and deploying the second stent off of the distal end of the guide tube alongside the first stent.

There is further provided in accordance with some applications of the present invention, apparatus including: a guide tube shaped to define a guidewire-engaging portion at a distal portion of the guide tube, a proximal end of the guidewire-engaging portion being located distally to a proximal end of the guide tube; a first stent surrounding the guide tube so as to be advanceable together with the guide tube into a lumen of a subject, the first stent being slidable along the guide tube such that a distal end of the first stent is disposed proximally to the guidewire-engaging portion of the guide tube; a guidewire arranged (i) entering a lumen of the guide tube from a distal-end opening of the guide tube, (ii) disposed in the guidewire-engaging portion, and (iii) passing out of the lumen of the guide tube proximally to the guidewire-engaging portion of the guide tube, such that the first stent is constrained from distal motion past the guidewire-engaging portion by the guidewire being disposed within the guidewire-engaging portion; and a second stent, proximal to the first stent, surrounding a proximal portion of the guide tube and the guidewire, and shaped and sized to be advanceable along the guide tube, and: (i) the guidewire is positioned to laterally exit the guidewire-engaging portion without being advanced distally or proximally, (ii) the first stent is slidably deployable off of the distal end of the guide tube upon the guidewire having exited the guidewire-engaging portion, without the guidewire having been moved proximally subsequent to the guidewire exiting the guidewire-engaging portion, and (iii) the second stent is slidably deployable off of the distal end of the guide tube and placeable alongside the first stent subsequently to deployment of the first stent off of the distal end of the guide tube, without the guidewire having been moved proximally subsequent to the guidewire exiting the guidewire-engaging portion.

For some applications, the first stent (a) has an outer surface disposed against the guidewire and (b) is configured to be advanced into the lumen of the subject while the outer surface is disposed against the guidewire. For some applications, the guidewire-engaging portion is shaped to define a slit extending proximally along a wall of the guide tube, from a distal end of the guide tube, the slit having a length of 1-70 mm. For some applications, the slit is shaped to define two slit lips that are in contact with each other to define a closed-slit configuration in the absence of any forces applied to the slit lips, and disengageable from each other, by application of a force to the lips, to define an opened-slit configuration. For some applications, the slit is shaped to define two slit lips that are in contact with each other to define a closed-slit configuration, and disengageable from each other to define an opened slit configuration, and further including a lock which: presses the slit lips against each other in the closed-slit configuration when the guidewire is disposed in the guidewire-engaging portion to inhibit the lateral exiting of the guidewire from the guidewire-engaging portion, and allows the lateral exiting of the guidewire from the guidewire-engaging portion in the opened-slit configuration when the lock does not press the slit lips against each other.

For some applications, the guidewire-engaging portion is shaped to define a weak spot configured to (i) tear in response to force applied to the weak spot by the guidewire upon the distal portion of the guide tube being withdrawn into the first stent, and (ii) shaped and sized to allow passage of the guidewire therethrough in the teared state thereof.

For some applications, the apparatus further includes: a first lock, which prevents proximal motion of the first stent past a location that is at least 1 mm from a distal end of the second stent; and a second lock, which prevents distal motion of the second stent past a location that is at least 1 mm proximal of a proximal end of the first stent. For some applications, the guide tube is shaped to define two holes in a lateral wall of the guide tube, and wherein the first lock includes a locking wire that passes through the two holes.

For some applications: the second stent is shaped to define a hole in a portion of the second stent, the apparatus further includes a pushing tube, disposed proximally to the second stent and configured to push the second stent off of the guide tube, the pushing tube is shaped to define a hole in a portion of the pushing tube, and the second lock includes a locking wire that passes through the hole in the portion of the second stent and through the hole in the portion of the pushing tube.

For some applications, the first lock includes a first locking wire, and wherein the second lock includes a second locking wire. For some applications, the first lock is configured to prevent distal motion of the first stent during advancement of the first stent on the guide tube into the lumen of the subject.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A stent-deployment assembly for use with a guidewire, comprising:
    a. a single biliary stent; and
    b. an elongated stent-conveyance tube comprising a guidewire-retaining segment that includes (i) respective distal and proximal apertures defining a guidewire-path therethrough, and (ii) a lengthways laterally-breachable portion,
    wherein:
        i. in a stent-advancement configuration, (A) the guidewire passes through the respective apertures so as to interiorly traverse the guidewire-retaining segment, (B) the stent is arranged to surround a stent-conveyance tube segment that is proximally displaced from the guidewire-retaining segment, for advancement of the stent together with the stent-conveyance tube along the guidewire into a body lumen of a human subject, and (C) the single stent is the only stent surrounding the stent-conveyance tube, and
        ii. when the stent is disposed, in the stent-advancement configuration, at a target deployment location within the lumen, a proximal-direction withdrawal of the stent-conveyance tube is effective to cause the guidewire to breach the laterally-breachable portion of the guidewire-retaining segment so as to decouple the guidewire from the stent-conveyance tube without longitudinal displacement of the guidewire.

2. The assembly of claim 1, wherein, when the assembly is advanced along the guidewire in the stent-advancement configuration, the guidewire-retaining segment is effective to retain the guidewire therewithin.

3. The assembly of claim 1, wherein a segment of the stent-conveyance tube proximally abutting the guidewire-retaining segment has a smaller diameter than does the guidewire-retaining segment.

4. The assembly of claim 1, wherein the distal aperture of the guidewire-retaining segment faces distally and the proximal aperture faces proximally.

5. The assembly of claim 1, additionally comprising a pushing tube and a proximally withdrawable locking mechanism, wherein the proximally-withdrawable locking mechanism engages the stent with the pushing tube and is effective to maintain a position of the stent relative to the stent-conveyance tube when the assembly is advanced along the guidewire in the stent-advancement configuration.

6. The assembly of claim 5, wherein a proximal-direction withdrawal of the stent-conveyance tube is effective to disengage the proximally-withdrawable locking mechanism.

7. The assembly of claim 1, wherein a proximal-direction withdrawal of the stent-conveyance tube after the lateral breaching of the laterally-breachable portion of the guidewire-retaining segment by the guidewire is effective to leave the stent deployed in the lumen without manipulation of the guidewire.

8. The assembly of claim 1, wherein the laterally-breachable portion of the guidewire-retaining segment includes a perforated portion and/or a thinned tube-wall portion.

9. A stent-deployment assembly for use with a guidewire, comprising:
    a. an elongated stent-conveyance tube comprising a guidewire-retaining segment (i) having a lengthways laterally-breachable portion and (ii) configured for having the guidewire traverse therethrough; and
    b. a single biliary stent arranged to surround a stent-conveyance tube segment that is proximally displaced from the guidewire-retaining segment, for advancement of the single stent together with the stent-conveyance tube along the guidewire into a body lumen of a human subject,
    wherein when the stent is disposed at a target deployment location within the lumen, a proximal-direction withdrawal of the stent-conveyance tube is effective to cause the guidewire to breach the laterally-breachable portion of the guidewire-retaining segment so as to decouple the guidewire from the stent-conveyance tube without manipulation of the guidewire.

10. The assembly of claim 9, wherein, when the assembly is advanced along the guidewire in the stent-advancement configuration, the guidewire-retaining segment is effective to retain the guidewire therewithin.

11. The assembly of claim 9, wherein a segment of the stent-conveyance tube proximally abutting the guidewire-retaining segment has a smaller diameter than does the guidewire-retaining segment.

12. The assembly of claim 9, additionally comprising a pushing tube and a proximally withdrawable locking mechanism, wherein the proximally-withdrawable locking mechanism engages the stent with the pushing tube and is effective to maintain a position of the stent relative to the stent-conveyance tube when the assembly is advanced along the guidewire in the stent-advancement configuration.

13. The assembly of claim 12, wherein a proximal-direction withdrawal of the stent-conveyance tube is effective to disengage the proximally-withdrawable locking mechanism.

14. The assembly of claim 9, wherein a proximal-direction withdrawal of the stent-conveyance tube after the lateral breaching of the laterally-breachable portion of the guidewire-retaining segment by the guidewire is effective to leave the stent deployed in the lumen without manipulation of the guidewire.

* * * * *